(12) United States Patent
Hecht et al.

(10) Patent No.: US 7,893,042 B2
(45) Date of Patent: Feb. 22, 2011

(54) PHENAZOPYRIDINE COMPOUNDS

(75) Inventors: Sidney Hecht, Phoenix, AZ (US); Nour Eddine Fahmi, Charlottesville, VA (US); Samir D. Roy, Los Altos, CA (US); George Bonneville, Stanardsville, VA (US)

(73) Assignee: Pinnacle Pharmaceuticals, Inc., Radford, VA (US)

( * ) Notice: Subject to any disclaimer, the term of this patent is extended or adjusted under 35 U.S.C. 154(b) by 0 days.

(21) Appl. No.: 12/645,099

(22) Filed: Dec. 22, 2009

(65) Prior Publication Data

US 2010/0204185 A1 Aug. 12, 2010

Related U.S. Application Data

(60) Provisional application No. 61/232,663, filed on Aug. 10, 2009, provisional application No. 61/139,428, filed on Dec. 19, 2008.

(51) Int. Cl.
*A61K 31/655* (2006.01)
*C07D 213/75* (2006.01)
*A61P 13/02* (2006.01)

(52) U.S. Cl. ..................... 514/150; 534/773
(58) Field of Classification Search ............ None
See application file for complete search history.

(56) References Cited

U.S. PATENT DOCUMENTS

| | | | |
|---|---|---|---|
| 3,493,555 | A | 2/1970 | Wilbert et al. |
| 3,950,321 | A | 4/1976 | Dehnert et al. |
| RE29,640 | E | 5/1978 | Lamm et al. |
| 4,829,070 | A | 5/1989 | Bodor |
| 5,567,716 | A * | 10/1996 | Della Valle et al. ......... 514/150 |
| 6,716,452 | B1 | 4/2004 | Piccariello et al. |
| 7,018,654 | B2 | 3/2006 | Kirk et al. |
| 7,060,708 | B2 | 6/2006 | Piccariello et al. |
| 7,427,600 | B2 | 9/2008 | Mickle et al. |
| 7,589,233 | B2 | 9/2009 | Chandran |
| 2004/0248963 | A1 | 12/2004 | Bueno Melendo et al. |
| 2006/0241017 | A1 | 10/2006 | Chandran |
| 2007/0196421 | A1 | 8/2007 | Hunter et al. |

FOREIGN PATENT DOCUMENTS

| | | | |
|---|---|---|---|
| JP | 01-193375 | A | 8/1989 |
| JP | 06-067467 | A | 3/1994 |
| JP | 2004-059687 | A | 2/2004 |
| WO | WO 2005/046575 | A2 | 5/2005 |
| WO | WO 2006/114324 | * | 11/2006 |
| WO | WO 2007/045829 | A2 | 4/2007 |

OTHER PUBLICATIONS

Jones, R.J. and Bischofberger, N., "Minireview: nucleotide prodrugs," *Antiviral Research* 27:1-17, Elsevier Science B.V., Netherlands (1995).

Notari, R.E., "Prodrug Design," *Pharmac. Ther.* 14:25-53, Pergamon Press Ltd., England (1981).

International Search Report for International Application No. PCT/US09/68963, mailed on Feb. 23, 2010, ISA/US, Alexandria, VA, USA.

Patent Abstracts of Japan, English language abstract for JP 01-193375 A, Japanese Patent Office, Patent & Utility Model Gazette DB (1989).

Patent Abstracts of Japan, English language abstract for JP 06-067467 A, Japanese Patent Office, Patent & Utility Model Gazette DB (1994).

Patent Abstracts of Japan, English language abstract for JP 2004-059687 A, Japanese Patent Office, Patent & Utility Model Gazette DB (2004).

Amit, G. and A. Halkin, "Lemon-yellow nails and long-term phenazopyridine use," *Ann. Intern. Med.* 127:1137, American College of Physicians, United States (1997).

Badley, B.W.D., "Phenazopyridine-induced hepatitis," *Br. Med. J.* 2:850, British Medical Assn., United Kingdom (1976).

Borisy, A.A., et al., "Systematic discovery of multicomponent therapeutics," *Proc. Natl. Acad. Sci. U.S.A.* 100:7977-7982, National Academy of Sciences, United States (2003).

Conroy, J.M., et al., "Acquired Methemoglobinemia From Multiple Oxidants," *South. Med. J.* 86:1156-1159, Southern Medical Assn., United States (1993).

Daly, J.S., et al., "Phenazopyridine induced methaemoglobinaemia associated with decreased activity of erythrocyte cytochrome b5 reductase," *J. Med. Genet.* 20:307-309, British Medical Assn., United Kingdom (1983).

Fincher, M.E., "Methemoglobinemia and Hemolytic Anemia After Phenazopyridine Hydrochloride (Pyridium) Administration in End-Stage Renal Disease," *South. Med. J.* 82:372-374, Southern Medical Assn., United States (1989).

(Continued)

*Primary Examiner*—Fiona T Powers
(74) *Attorney, Agent, or Firm*—Sterne, Kessler, Goldstein & Fox P.L.L.C.

(57) ABSTRACT

The present invention is directed to substituted phenazopyridines represented by Formula I. The present invention also relates to the discovery that compounds of Formula I have increased bioavailability as compared to unconjugated phenazopyridine.

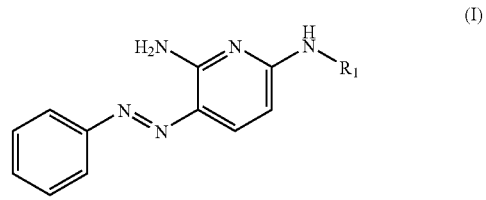

(I)

33 Claims, 18 Drawing Sheets

OTHER PUBLICATIONS

Galloway, S.M., et al., "Chromosome Aberrations and Sister Chromatid Exchanges in Chinese Hamster Ovary Cells: Evaluations of 108 Chemicals," *Environ. Mol. Mutagen.* 10:1-32, 91, and 93, Alan R. Liss, Inc., United States (1987).

S.E. Goldfinger and S. Marx, "Hypersensitivity Hepatitis Due to Phenazopyridine Hydrochloride," *N. Engl. J. Med.* 286:1090-1091, Massachusetts Medical Society, United States (1972).

Haigh, C. And J. C. Dewar, "Multiple Adverse Effects of Pyridium: A Case Report," *South. Med. J.* 99:90-92, Southern Medical Assn. United States (2006).

Landman, J., et al., "Acquired Methemoglobinemia Possibly Related to Phenazopyridine in a Woman with Normal Renal Function," *J. Urol.* 158: 1520-1521, American Urological Assn., Inc., United States (1997).

Li, K-j., et al., "Determination of Phenazopyridine in Human Plasma by GC-MS and its Pharmacokinetics," *J. Chromatogr. Sci.* 46:686-689, Preston Technical Abstracts, United States (2008).

Lin, T.E., "Phenazopyridine Monograph," (Dissertation), University of New Mexico College of Pharmacy, Clinical Toxicology APPE, Jan. 2008, 15 pages.

Mercieca, J.E., et al., "Acute Haemolytic Anaemia Due to Phenazopyridine Hydrochloride in G-6-PD Deficient Subject," *The Lancet 320*:564, Elsevier, United Kingdom (1982).

Mortelmans, K., "*Salmonella* Mutagenicity Tests: II. Results From the Testing of 270 Chemicals," *Environmental Mutagenesis 8*:1-3, 9, 36, 39, and 97, Alan R. Liss, Inc., United States (1986).

Randazzo, G.P., et al., "Methemoglobinemia Caused by Acute Overdosage of Phenazopyridine," *West. J. Med.* 122:427-429, BMJ Publishing, United Kingdom (1975).

Shang, E., "Determination of phenazopyridine in human plasma via LC-MS and subsequent development of a pharmacokinetic model," *Anal. Bioanal. Chem.* 382:216-222, Springer-Verlag, Germany (2005).

Shi, C-W., et al., "Usage Patterns of Over-the-counter Phenazopyridine (Pyridium)," *J. Gen. Intern. Med.* 18:281-287, Springer, United States (2003).

Shi, C-W., et al., "Consumer Knowledge of Over-the-Counter Phenazopyridine," *Ann. Fam. Med.* 2:240-244, Annals of Family Medicine, Inc., United States (2004).

Shreve, R.N., et al., "Studies in Azo Dyes. I. Preparation and Bacteriostatic Properties of Azo Derivatives of 2,6-Diaminopyridine," *J. Am. Chem. Soc.* 65:2241-2243, American Chemical Society, United States (1943).

Slatter, D.H., et al., "Toxicity of Phenazopyridine," *Arch. Opthalmol.* 91:484-486, American Medical Assn., United States (1974).

Thomas, B.H., "Excretion of Phenazopyridine and Its Metabolites in the Urine of Humans, Rats, Mice, and Guinea Pigs," *J. Pharm. Sci.* 79:321-325, American Pharmaceutical Assn., United States (1990).

Thomas, B.H., "Metabolism and disposition of phenazopyridine in rat," *Xenobiotica 23*:99-105, Taylor and Francis Ltd, United Kingdom (1993).

J.T. Wilde and A.G. Prentice, "Sulfamethoxazole-Phenazopyridine and Thrombocytope," *Ann. Intern. Med.* 104:128-129, American College of Physicians, United States (1986).

"Bioassay of Phenazopyridine Hydrochloride for Possible Carcinogenicity," National Cancer Institute, Carcinogenesis Technical Report Series No. 99, National Institutes of Health, United States (1978).

"Phenazopyridine Hydrochloride CAS No. 136-40-3," Report on Carcinogens, 11th ed., U.S. Department of Health and Human Services, Public Health Service, National Toxicology Program, 1 page (1981).

* cited by examiner

| Compound State | Solvent | | | | |
|---|---|---|---|---|---|
| | H₂O | CH₃OH | CH₃CH₃OH | AcOAc | 0.1% AcOH H₂O |
| Free Base | — | ✓ | ✓ | ✓ | ✓ |
| HCl Salts | <10mg/ml | ✓✓ | ✓✓ | — | ✓✓ |

Figure 5.

| Salt | Soluble (mg/mL) | maxsoluble (mg/mL) | AUC* (ng-h/mL) |
|---|---|---|---|
| HCl | 8.5 | <10.0 | 439 |
| HBr | 2.3 | <3.0 | 252 |
| mesylate | 80.2 | >80.2 | 153 |
| salicylate | 0.1 | <0.2 | 351 |
| PAP-HCl | 1.2 | <1.5 | 100 |

*In rats administered by oral (adjusted to 2.5 mg/kg of PAP-free base equivalent dose)

Figure 6.

| Stability study of Gly-PAP by UV-HPLC | | | | | | | | | |
|---|---|---|---|---|---|---|---|---|---|
| compound states | | purity (area%) | | | | | | | |
| | | at 40 °C (day) | | | | | | at room temp (day) | |
| | | 0st | 1st | 2nd | 3rd | 4th | 5th | 14th | 75th | 90th |
| free base | solid | 99.6 | 99.3 | 99.2 | 99 | 98.7 | 98.5 | 96.3 | 99.3 | 99.2 |
| HCl salt | solution in water | 98.4 | 81.9 | 67.8 | 56.8 | 47.3 | 38.2 | - | (98.2 at 4h) | (91.8 at 3 days) |
| | | | | | | | | | (98.1 at 8h) | (90.0 at 4 days) |
| | | | | | | | | | (96.5 at 1 day) | 87.3 at 5 days |
| | | | | | | | | | (94.6 at 2 days) | (74.3 at 14 days) |
| | solid | 98.4 | 98.4 | 98.3 | 98.2 | 98.1 | 98.1 | 97.9 | 98.3 | 98.3 |

Figure 7.

| T (time, h/d) | purity (area %) |
|---|---|
| T-0 | 98.33 |
| T-4h | 98.31 |
| T-8h | 98.26 |
| T-1d | 98.08 |
| T-2d | 97.88 |
| T-4d | 96.69 |
| T-6d | 96.01 |
| T-8d | 95.32 |

*Concentration of Gly-PAP in water: 0.2 mg/mL

Figure 8.

| T (time, h/d) | purity (area %) |
|---|---|
| T-0 | 98.67 |
| T-4h | 98.42 |
| T-8h | 98.25 |
| T-1d | 97.76 |
| T-2d | 97.12 |
| T-4d | 95.78 |
| T-6d | 94.71 |
| T-8d | 93.45 |

*Concentration of Gly-PAP in water: 8.8 mg/mL

Figure 9.

| T (time, h) | purity (area %) |
|---|---|
| T-0 | 98.4 |
| T-4 | 98.2 |
| T-8 | 98.1 |
| T-24 | 96.5 |
| T-48 | 94.6 |

Figure 10.

Summary of Phenazopyridine Pharmacokinetics Following Oral Administration of Gly-PAP or Phenazopyridine HCl in Male Rats

| Test Article | Dose (mg/kg) | Dose Phenazopyridine base (mg/kg) | $C_{max}$ (ng/mL) | $AUC_{0-24}$ (ng.h/mL) |
|---|---|---|---|---|
| Gly-PAP (n=2) | 4 | 2.5 | 139.5 ± 0.71 | 368.2 ± 13.7 |
| Phenazopyridine HCl (n=2) | 2.8 | 2.5 | 55.8 ± 10.7 | 113.6 ± 22.1 |
| Gly-PAP (n=3) | 0.9 | 0.6 | 48.5 ± 3.5 | 122.2 ± 2.4 |

Figure 11.

Summary of Gly-PAP Pharmacokinetics Following Oral Administration of Gly-PAP in Male Rats

| Test Article | Dose (mg/kg) | Dose Phenazopyridine base (mg/kg) | $C_{max}$ (ng/mL) | $AUC_{0-24}$ (ng.h/mL) |
|---|---|---|---|---|
| Gly-PAP (n=2) | 4 | 2.5 | 6.4 | 13.7 ± 0.7 |
| Gly-PAP (n=3) | 0.9 | 0.6 | 2.7 | 5.8 ± 0.6 |

Figure 12.

| Animal Number | Group | $T_{max}$ (Hours) | $C_{max}$ (ng/mL) | $AUC_{0-t}$ (Hour·ng/mL) | $AUC_{0-inf}$ (Hour·ng/mL) | $t_{1/2}$ (Hours) |
|---|---|---|---|---|---|---|
| | | | GLY-PAP | | | |
| CXUBBN | 1 | 2 | 36.2 | 104 | 107 | 1.34 |
| CWTBIC | 1 | 1 | 20.4 | 41.8 | 44.1 | 0.846 |
| CXNATX | 1 | 0.5 | 78.1 | 193 | 196 | 1.33 |
| | Mean | 1.17 | 44.9 | 113 | 116 | 1.17 |
| | SD | 0.76 | 29.8 | 76 | 77 | 0.28 |
| | | | PAP | | | |
| CXUBBN | 1 | 2 | 250 | 708 | 716 | 1.09 |
| CWTBIC | 1 | 1 | 263 | 604 | 608 | 1.09 |
| CXNATX | 1 | 2 | 968 | 3100 | 3100 | 1.12 |
| | Mean | 1.67 | 494 | 1471 | 1475 | 1.10 |
| | SD | 0.58 | 411 | 1412 | 1409 | 0.02 |
| | | | PAP | | | |
| CVVCVD | 2 | 1 | 924 | 1850 | 1850 | 1.41 |
| CTZBCG | 2 | 0.5 | 2510 | 3210 | 3220 | 1.3 |
| CYMAKV | 2 | 0.5 | 1570 | 1730 | 1730 | 0.879 |
| | Mean | 0.667 | 1668 | 2263 | 2267 | 1.20 |
| | SD | 0.289 | 798 | 822 | 828 | 0.28 |

$AUC_{0-t}$ Area under the plasma concentration-time curve up to the last sampling time with measurable concentrations.
$AUC_{0-inf}$ Area under the plasma concentration-time curve up to infinity.
$C_{max}$ Maximum plasma concentration.
SD Standard deviation.
$T_{max}$ Time to maximum concentration.
$t_{1/2}$ Observed elimination half-life.

Figure 14.

| Animal Number | Group | Concentration (ng/mL) Collection Interval (Hours) | | 0 to 24-Hour Total Urine Volume (mL) | 0 to 24-Hour Total Urine Output (ng)[a] |
|---|---|---|---|---|---|
| | | Predose (-18 to 0) | 0 to 24 | | |
| *GLY-PAP* | | | | | |
| CXUBBN | 1 | BLQ | BLQ | 260 | 0.00 |
| CWTBIC | 1 | BLQ | BLQ | 375 | 0.00 |
| CXNATX | 1 | BLQ | 15.8 | 175 | 2765 |
| | Mean | 0.00 | 5.27 | | 922 |
| | SD | 0.00 | 9.12 | | 1596 |
| *PAP* | | | | | |
| CXUBBN | 1 | BLQ | 18.4 | 260 | 4784 |
| CWTBIC | 1 | BLQ | 12.0 | 375 | 4500 |
| CXNATX | 1 | BLQ | 31.0 | 175 | 5425 |
| | Mean | 0.00 | 20.5 | | 4903 |
| | SD | 0.00 | 9.7 | | 470 |
| CVVCVD | 2 | BLQ | 16.5 | 200 | 3300 |
| CTZBCG | 2 | BLQ | 9.51 | 280 | 2663 |
| CYMAKV | 2 | BLQ | 8.56 | 190 | 1626 |
| | Mean | 0.00 | 11.5 | | 2530 |
| | SD | 0.00 | 4.3 | | 850 |

BLQ  Below the limit of quantitation (5.00 ng/mL). Considered as zero for calculation of mean and SD.
PAP  Phenazopyridine.
SD   Standard deviation.
Note: Group 1 received GLY-PAP (8.1 mg/kg). Group 2 received PAP HCl (5.9 mg/kg).
a    Calculated using the Total Urine Volume × Concentration (ng/mL).

Figure 15.

Synthetic Scheme

| Compound | Dose (mg/kg) | PAP base equivalent | Cmax (ng/mL) | AUC0-6 (ng.h/mL) |
|---|---|---|---|---|
| Gly-PAP HCl | 4 | 2.5 | 139.5 | 368.2 ± 13.7 |
| Gly-PAP mesylate | 5.4 | 2.5 | 104.9 | 244.7 ± 55.5 |
| Gly-PAP HBr | 5 | 2.5 | 63.7 | 148.3 ± 27.0 |
| Gly-PAP salicylate | 7.1 | 3.7 | 146.9 | 505.9 ± 47.1 |
| PAP HCl | 2.9 | 2.5 | 58.9 | 97.2 ± 25.4 |

Figure 17.

Observations of Emesis in Dogs Administered Equivalent Phenazopyridine Containing Doses of Gly-PAP or Phenazopyridine HCl TID (3 doses given 8h apart)

| Test Article | Group No. (sex) | Dose (mg.kg) | Phenazopyridine Base (mg/kg) | Dose No. | Vomitus Observed |
|---|---|---|---|---|---|
| Gly-PAP | 1 (male) | 40 | 24.8 | 1 | None |
| Gly-PAP | 1 (female) | 40 | 24.8 | 1 | None |
| Gly-PAP | 1 (male) | 40 | 24.8 | 2 | None |
| Gly-PAP | 1 (female) | 40 | 24.8 | 2 | None |
| Gly-PAP | 1 (male) | 40 | 24.8 | 3 | None |
| Gly-PAP | 1 (female) | 40 | 24.8 | 3 | 4h post-dose |
| Phenazopyridine HCl | 2 (male) | 29.1 | 24.8 | 1 | None |
| Phenazopyridine HCl | 2 (female) | 29.1 | 24.8 | 1 | 4h post-dose |
| Phenazopyridine HCl | 2 (male) | 29.1 | 24.8 | 2 | 4h-post dose |
| Phenazopyridine HCl | 2 (female) | 29.1 | 24.8 | 2 | None |
| Phenazopyridine HCl | 2 (male) | 29.1 | 24.8 | 3 | 4-h post dose |
| Phenazopyridine HCl | 2 (female) | 29.1 | 24.8 | 3 | 1 and 4h post-dose |

Figure 18.

PHENAZOPYRIDINE COMPOUNDS

BACKGROUND OF THE INVENTION

1. Field of the Invention

The invention describes phenazopyridine covalently attached to various conjugates. These compounds and compositions are useful for providing increased (oral) bioavailability with reduced side effects.

2. Related Art

Various publications are cited herein, the disclosures of which are incorporated by reference in their entireties. However, the citation of any reference herein should not be construed as an admission that such reference is available as prior art to the present application.

Phenazopyridine is an analgesic compound indicated for urinary tract pain, burning, irritation, and discomfort, as well as urgent and frequent urination caused by urinary tract infections, surgery, injury, or examination procedures. Phenazopyridine, while an effective analgesic, carries with it a foreboding side effect profile, with nausea, vomiting, and general GI upset being the most severe events. In an effort to improve the side effect profile and expand the use of phenazopyridine, it is proposed to pursue the development of a prodrug compound that results in the formation of the active drug following transport across the gastrointestinal epithelium.

Phenazopyridine or 2,6-pyridinediamine, 3-(phenylazo), monochloride (CAS number 94-78-0) is an azo dye that exerts topical analgesic or local anesthetic action on the urinary tract mucosa and provides symptomatic relief of pain, burning, urgency, frequency and other discomforts arising from irritation of lower urinary tract caused by infections, trauma, surgery, endoscopic procedures or use of catheters. Phenazopyridine has been marketed since 1925 and since 1951 has had a dual status of prescription and over-the-counter (OTC).

Phenazopyridine is marketed as single agent 100 and 200 mg tablets under a number of brand names including Nefrecil, Phenazodine, Pyridiate, Pyridium, Sedural, Uricalm, Uropyrine, Urodine, and Urogesic. Single agent OTC medications include Azo-Gesic, Azo-Standard, and Uristat (95 mg tablets), ReAzo (97 mg tablets), and URIRelief and Baridium (97.2 mg tablets). Phenazopyridine is available as a combined prescription with sulfisoxazole or sulfamethoxazole/trimethoprim and as Phenazopyridine plus in combination with hyosciamine and secbarbitol.

The usual adult dosage is 100-200 mg three times daily after meals for no more than two days and 12 mg/kg/day in three divided doses after meals in children for no more than two days. The pharmacological mechanism of the analgesic effect of phenazopyridine is unknown.

Phenazopyridine is absorbed from the gastrointestinal tract following oral administration. Although the absolute bioavailability in humans has not been determined it is apparently poorly absorbed with the highest prescribed dose of 200 mg yielding maximum plasma levels between 10 and 20 ng/mL. Phenazopyridine is rapidly excreted up to 65% unchanged in urine with approximately 90% of a single dose cleared within 24 hours. Metabolites include aniline, N-acetyl-p-aminophenol (NAPA or acetaminophen) and p-amino phenol. Aniline may contribute to the analgesic effect of orally administered phenazopyridine in the urinary tract mucosa.

Adverse reactions associated with therapeutic doses of phenazopyridine include headache, rash pruritus, gastrointestinal disturbances (nausea, vomiting, and diarrhea), orange to red urine discoloration and staining of soft contact lenses. In cases of insufficient renal clearance phenazopyridine can tinge skin, sclera or fluids yellow due to accumulation of the drug. Methemaglobenemia, hemolytic anemia, renal and hepatic toxicity have been reported, usually at overdose levels. Anaphylactoid reactions have been reported.

Phenazopyridine and the metabolite aniline can cause oxidative stress within red blood cells by conversion of hemoglobin to methemaglobin. Patients with glucose-6-phosphate dehydrogenase deficiency may be predisposed to hemolytic anemia. Phenazopyridine should not be administered to patients with impaired renal function. Exceeding the recommended dose may lead to increased serum levels and toxic reactions. Methemaglobinemia generally follows excessive acute overdose. Considering the long history and fairly widespread use of phenazopyridine, reports of serious toxicity are relatively uncommon.

Long term (2 years) administration of phenazopyridine hydrochloride induced adenomas and adenocarcinomas in the large intestine of rats and lifetime administration caused hepatocellular adenomas and carcinomas in female mice. Phenazopyridine has been shown to be mutagenic in bacteria and mutagenic and clastogenic in mammalian cells. In one limited epidemiological study of 2,214 patients who received phenazopyridine hydrochloride there was no observed increase in the occurrence of any type of cancer over a minimum period of 3 years. Current phenazopyridine product labeling indicates: "Long term administration of phenazopyridine hydrochloride has induced neoplasia in rats (large intestine) and mice (liver). Although no association between phenazopyridine hydrochloride and human neoplasia has been reported, adequate epidemiological studies along these lines have not been conducted."

Reproduction studies at doses up to 50 mg/kg/day or 110 mg/kg/day in rats and 39 mg/kg/day in rabbits showed no effects on fertility or embryo-fetal development. Phenazopyridine is currently classified in pregnancy category B. There have been no adequate and well controlled studies of phenazopyridine exposure in pregnant women. Surveillance studies have been reported with no link of phenazopyridine use to congenital defects. The Collaborative Perinatal Project monitored 50,282 mother-child pairs with 1,109 exposures recorded during pregnancy and 219 exposures during the first trimester. No association was found with major or minor malformations or individual defects. Surveillance of 229,101 Michigan Medicaid patents identified 469 phenazopyridine exposures during the first trimester. No data was obtained to indicate any association of the drug with abnormalities.

The acute toxicity LD50 for phenazopyridine has been reported as 472 mg/kg (oral) and 200 (i.p.) in rats; and 180 mg/kg (i.p.) in mice. Adequate safety pharmacology and repeat dose nonclinical toxicology studies have not been performed for phenazopyridine.

BRIEF SUMMARY OF THE INVENTION

The invention provides covalent attachment of phenazopyridine and derivatives or analogs thereof to a variety of chemical moieties. The chemical moieties may include any substance which results in a prodrug form, i.e., a molecule which is converted into its active form in the body by normal metabolic processes. For example, the chemical moieties may be single amino acids, dipeptides, or polypeptides.

The chemical moiety is covalently attached either directly or indirectly through a linker to the phenazopyridine. The site of attachment is typically determined by the functional group(s) available on the phenazopyridine.

In one embodiment, the phenazopyridine is attached to a single amino acid which is either naturally occurring or a synthetic amino acid. In another embodiment, the phenazopyridine is attached to a dipeptide or tripeptide, which could be any combination of the naturally occurring amino acids and synthetic amino acids. In another embodiment, the amino acids are selected from L-amino acids for digestion by proteases.

Other objects, advantages and embodiments of the invention are described below and will be obvious from this description and practice of the invention.

BRIEF DESCRIPTION OF DRAWINGS

FIG. 5 is a table showing the solubility of Gly-PAP at room temperature as a free base and HCl salt.

FIG. 6 is a table showing the solubility of Gly-PAP salts in water and bioavailability in rats.

FIG. 7 is a table showing the results of a stability study of Gly-PAP by UV-HPLC.

FIG. 8 is a table showing the results of a stability study of Gly-PAP-HCl in water solution at 4° C. by UV-HPLC at 0.2 mg/ml.

FIG. 9 is a table showing the results of a stability study of Gly-PAP-HCl in water solution at 4° C. by UV-HPLC at 8.8 mg/ml.

FIG. 10 is a table showing the results of a stability study of Gly-PAP-HCL in water solution at room temperature by UV-HPLC.

FIG. 11 is a table summary of phenazopyridine pharmacokinetics following oral administration of Gly-PAP or phenazopyridine HCl in male rats.

FIG. 12 is a table summary of Gly-PAP pharmacokinetics following oral administration of Gly-PAP in male rats.

FIG. 14 is a table summary of pharmacokinetic parameters in plasma collected from male dogs following a single oral administration of Gly-PAP (Group 1) or PAP HCl (Group 2).

FIG. 15 is a table summary of concentrations of PAP and Gly-PAP in urine following a single oral dose of Gly-PAP (Group 1) or PAP HCl (Group 2) to male dogs.

FIG. 17 is a table demonstrating oral bioavailability of Gly-PAP salts in rats.

FIG. 18 is a table demonstrating reduction of the GI side effect of emesis.

DETAILED DESCRIPTION OF THE INVENTION

Figure 1:
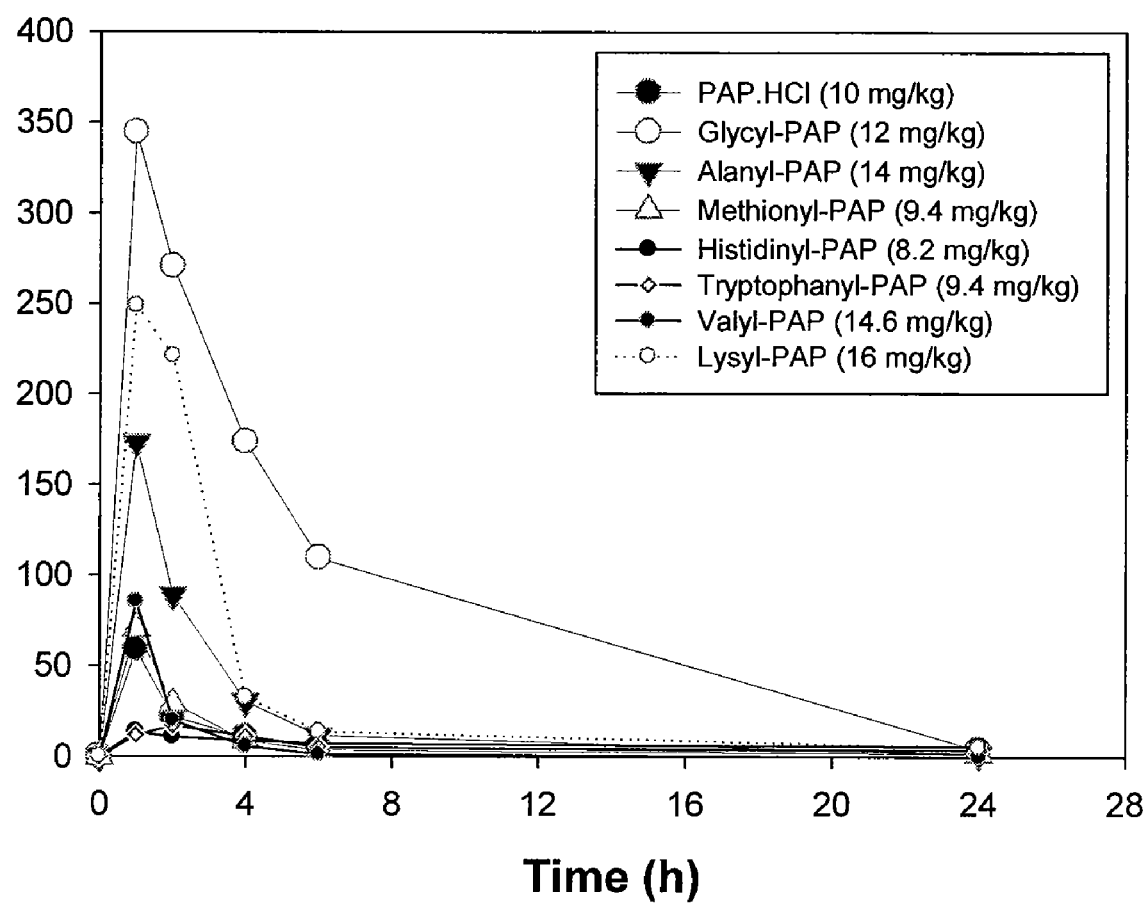
FIG. 1 is a graph showing the plasma concentrations of various phenazopyridine-amino acid conjugates in rats following oral administration of the phenazopyridine conjugates. Phenazopyridine (PAP) plasma concentrations versus time profiles are shown following administration of PAP.HCl, Gly-PAP, alanyl-PAP, methionyl-PAP, histidinyl-PAP, tryptophanyl-PAP, valyl-PAP, and lysyl-PAP.
Figure 2:
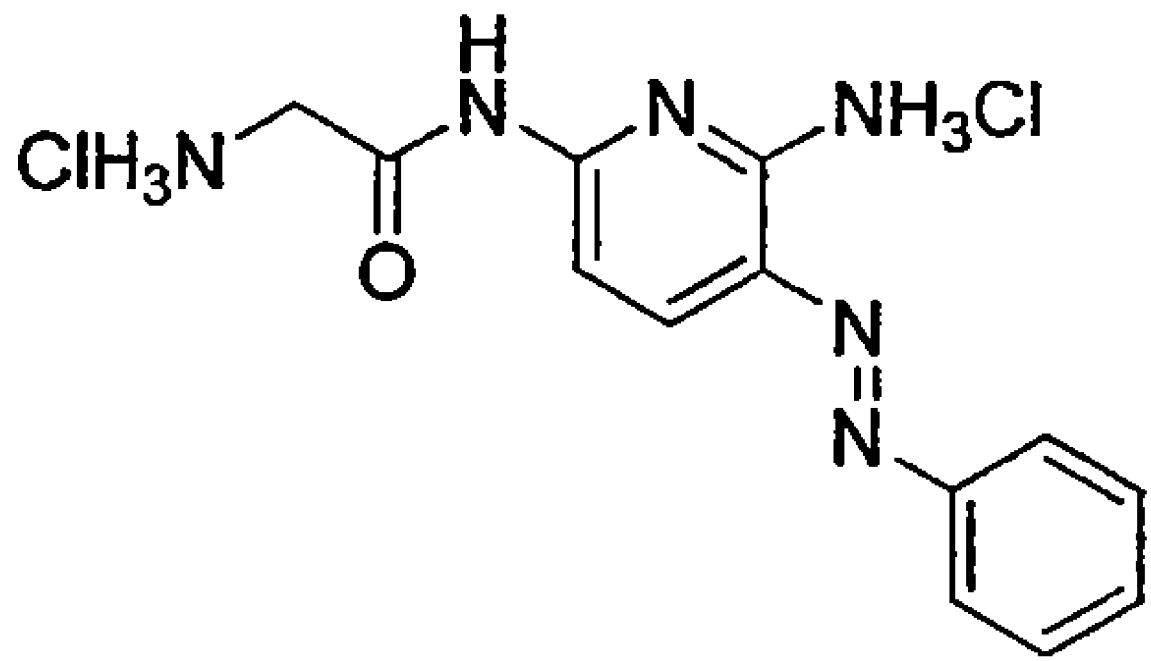
FIG. 2 is a depiction of 2-amino-6-aminoacetamido-3-E-phenazopyridine dihydrochloride.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, polypeptide or carrier peptide to illustrate specific embodiments for the active agent conjugate. Preferred lengths of the conjugates and other preferred embodiments are described herein.

A "composition" as used herein refers broadly to any composition containing a described molecule conjugate(s). The composition may comprise a dry formulation, an aqueous solution, or a sterile composition. Compositions comprising the molecules described herein may be stored in freeze-dried form and may be associated with a stabilizing agent such as a carbohydrate. In use, the composition may be deployed in an aqueous solution containing salts, e.g., NaCl, detergents, e.g., sodium dodecyl sulfate (SDS), and other components.

"Phenazopyridine" shall mean:

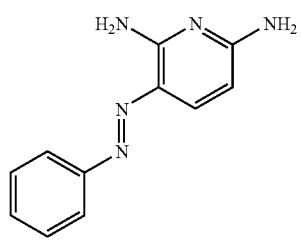

Compounds useful in the present invention are represented by Formula I:

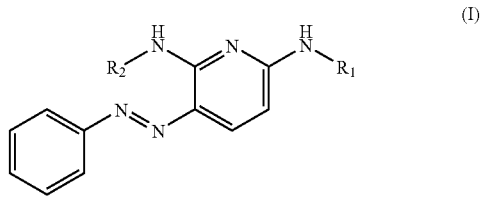

wherein, $R_1$ and $R_2$ are independently (a) hydrogen;

(b) the residue of an amino acid or peptide;

(c)

wherein $R_3$ is an optionally substituted alkyl or arylalkyl; or (d) the residue of an amino acid wherein the amine of the amino acid is protected with a t-butylcarbonyl;

wherein at least one of $R_1$ and $R_2$ is other than hydrogen.

This patent is meant to cover all compounds discussed regardless of absolute configurations. Thus, natural, L-amino acids are discussed but the use of D-amino acids are also included.

Use of the phrases such as, "decreased", "reduced", "diminished" or "lowered" is meant to include at least a 10% change in side effects with greater percentage changes being preferred. For instance, the change may also be greater than 25%, 35%, 45%, 55%, 65%, 75%, 85%, 95%, 96%, 97%, 98%, 99%, or increments therein.

The purity of the prodrug will preferably be greater than 25%, 35%, 45%, 55%, 65%, 75%, 85%, 90%, 95%, 96%, 97%, 98%, 99%, or increments therein.

The term increments is shall include without limitation, ones, tens, and fractions thereof, for instance, 1, 2, 3, 4, . . . or 0.1, 0.2, 0.3, 0.4 etc.

For each of the recited embodiments, the amino acid or peptide may comprise one or more of glycine or of the naturally occurring (L-) amino acids: alanine, arginine, asparagine, aspartic acid, cysteine, glutamic acid, glutamine, histidine, isoleucine, leucine, lysine, methionine, proline, phenylalanine, serine, tryptophan, threonine, tyrosine, and valine. In another embodiment, the amino acid or peptide is comprised of one or more of glycine or of the naturally occurring (D) amino acids: alanine, arginine, asparagine, aspartic acid, cysteine, glutamic acid, glutamine, histidine, isoleucine, leucine, lysine, methionine, proline, phenylalanine, serine, tryptophan, threonine, tyrosine, and valine. In another embodiment, the amino acid or peptide is comprised of one or more unnatural, non-standard or synthetic amino acids such as, aminohexanoic acid, biphenylalanine, cyclohexylalanine, cyclohexylglycine, diethylglycine, dipropylglycine, 2,3-diaminopropionic acid, homophenylalanine, homoserine, homotyrosine, naphthylalanine, norleucine, ornithine, (4-fluoro)phenylalanine, (2,3,4,5,6 pentafluoro) phenylalanine, (4-nitro)phenylalanine, phenylglycine, pipecolic acid, sarcosine, tetrahydroisoquinoline-3-carboxylic acid, and tert.-leucine. In another embodiment, the amino acid or peptide comprises one or more amino acid alcohols, for example, serine and threonine. In another embodiment the amino acid or peptide comprises one or more N-methyl amino acids, for example, N-methylaspartic acid. In another embodiment, the amino acid or peptide comprises one or more cyclic amino acids, for example, cis-4-hydroxy-D-proline.

In another embodiment, the specific carriers are utilized as a base short chain amino acid sequence and additional amino acids are added to the terminus or side chain. In another embodiment, the above amino acid sequence may have one more of the amino acids substituted with one of the 20 naturally occurring amino acids. It is preferred that the substitution be with an amino acid which is similar in structure or charge compared to the amino acid in the sequence. For instance, isoleucine (Ile)[I] is structurally very similar to leucine (Leu)[L], whereas, tyrosine (Tyr)[Y] is similar to phenylalanine (Phe)[F], whereas serine (Ser)[S] is similar to threonine (Thr)[T], whereas cysteine (Cys)[C] is similar to methionine (Met)[M], whereas alanine (Ala)[A] is similar to valine (Val)[V], whereas lysine (Lys)[K] is similar to arginine (Arg)[R], whereas asparagine (Asn)[N] is similar to glutamine (Gln)[Q], whereas aspartic acid (Asp)[D] is similar to glutamic acid (Glu)[E]. In the alternative, the preferred amino acid substitutions may be selected according to hydrophilic properties (i.e., polarity) or other common characteristics associated with the 20 essential amino acids. While preferred embodiments utilize the 20 natural amino acids for their GRAS characteristics, it is recognized that minor substitutions along the amino acid chain which do not affect the essential characteristics of the amino acid chain are also contemplated.

In one embodiment, the carrier range is between one to 12 chemical moieties with one to 8 moieties being preferred. In another embodiment, the number of chemical moieties is selected from 1, 2, 3, 4, 5, 6, or 7.

Formulations of the invention suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film-coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market need, i.e., unit dose, rolls, bulk bottles, blister packs, etc.

The invention also contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

It should be understood that in addition to the ingredients particularly mentioned above, the formulations of this invention can include other suitable agents such as flavoring agents, preservatives and antioxidants. Such antioxidants would be food acceptable and could include vitamin E, carotene, BHT or other antioxidants known to those of skill in the art.

Other compounds which may be included by admixture are, for example, medically inert ingredients, e.g., solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or lauryl sulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable or necessary, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. The suspensions and the emulsions may contain a carrier, for example a natural gum, agar, sodium alginate, pectin, methylcellulose, carboxymethylcellulose or polyvinyl alcohol.

The dose range for adult human beings will depend on a number of factors including the age, weight and condition of the patient. Tablets and other forms of presentation provided in discrete units conveniently contain a daily dose, or an appropriate fraction thereof, of one or more of the compounds of the invention. For example, units may contain from 5 mg to 500 mg, but more usually from 10 mg to 250 mg, of one or more of the compounds of the invention.

It is also possible for the dosage form to combine any forms of release known to persons of ordinary skill in the art. These include immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is known in the art.

Compositions of the invention may be administered in a partial, i.e., fractional dose, one or more times during a 24 hour period, a single dose during a 24 hour period of time, a double dose during a 24 hour period of time, or more than a double dose during a 24 hour period of time. Fractional, double or other multiple doses may be taken simultaneously or at different times during the 24 hour period. The doses may be uneven doses with regard to one another or with regard to the individual components at different administration times.

Likewise, the compositions of the invention may be provided in a blister pack or other such pharmaceutical package. Further, the compositions of the present inventive subject matter may further include or be accompanied by indicia allowing individuals to identify the compositions as products for a prescribed treatment. The indicia may additionally include an indication of the above specified time periods for administering the compositions. For example, the indicia may be time indicia indicating a specific or general time of day for administration of the composition, or the indicia may be a day indicia indicating a day of the week for administration of the composition. The blister pack or other combination package may also include a second pharmaceutical product.

It will be appreciated that the pharmacological activity of the compositions of the invention can be demonstrated using standard pharmacological models that are known in the art. Furthermore, it will be appreciated that the inventive compositions can be incorporated or encapsulated in a suitable polymer matrix or membrane for site-specific delivery, or can be functionalized with specific targeting agents capable of effecting site specific delivery. These techniques, as well as other drug delivery techniques, are well known in the art.

In another embodiment of the invention, the solubility and dissolution rate of the composition is substantially changed under physiological conditions encountered in the intestine, at mucosal surfaces, or in the bloodstream. In another embodiment the solubility and dissolution rate substantially decrease the bioavailability of the phenazopyridine, particularly at doses above those intended for therapy.

For each of the described embodiments, one or both of the following characteristics may be realized: The toxicity or side effects associated with the phenazopyridine conjugate are substantially lower than that of phenazopyridine itself. Some of the additional proposed benefits include the fact that the prodrug is hydrolyzed following oral administration, resulting in increased bioavailability, Tmax increase, increased polarity and solubility, and possible active transport by PepT1 or other transporters. As such benefits of the prodrug may also provide reduced GI exposure to PAP (and commensurate reduction in side effects), a reduced total dose and longer duration of action.

Another embodiment of the present invention provides phenazopyridine covalently bound to any single amino acid which include the twenty naturally occurring amino acids such as isoleucine, leucine, lysine, methionine, phenylalanine, threonine, tryptophan, valine, alanine, asparagine, aspartate, cysteine, glutamate, glutamine, glycine, proline, serine, tyrosine, arginine, or histidine.

In another embodiment, phenazopyridine is covalently bound to a dipeptide or a polypeptide.

In another embodiment, phenazopyridine is covalently bound to glycine.

In another embodiment, phenazopyridine is covalently bound to at least one glycine and an additional amino acid.

In another embodiment, phenazopyridine conjugates of the present invention are administered in a therapeutically effective amount to a patient to treat, for example, urinary tract pain, burning, irritation, discomfort, or urgent or frequent urination caused by urinary tract infections, surgery, injury, or examination procedures, wherein the amount administered to the patient is 90%, 80%, 70%, 60%, 50%, 40%, 30%, 20%, 10%, 5%, 1%, or other fractional amount of the standard dose of unconjugated phenazopyridine that would be administered according to standard clinical protocols.

In one embodiment, the phenazopyridine conjugates of the present invention are administered to a patient and the levels of observed side effects such as, for example, nausea, vomiting, and general GI upset, are reduced by 5%, 10%, 15%, 20%, 25%, 30%, 35%, 40%, 45%, 50%, or more relative to the levels of side effects observed when a standard dose of phenazopyridine is administered to a patient.

For each of the recited embodiments, covalent attachment may comprise an amide or carbamate bond.

The abbreviations used herein have their conventional meaning within the chemical and biological arts, unless otherwise specified. For example: "h" or "hr" means hour(s), "min" means minute(s), "sec" means second(s), "d" means day(s), "µL" means microliter(s), "mL" means milliliter(s), "L" means liter(s), "µM" means micromolar, "mM" means millimolar, "M" means molar, "mol" means mole(s), "mmol" means millimole(s), "µg" means microgram(s), "mg" means milligram(s), "×g" means times gravity, "aa" means amino acid(s), "k" means kilo, "µ" means micro, "° C." means degrees Celsius, "THF" means tetrahydrofuran, "DME" means dimethoxyethane, "DMF" means dimethylformamide, "NMR" means nuclear magnetic resonance, "BOC" means t-butoxycarbonyl, "psi" refers to pounds per square inch, and "TLC" means thin layer chromatography.

The term "alkyl" as used herein by itself or part of another group refers to a straight-chain, branched, or cyclic saturated aliphatic hydrocarbon having from one to ten carbons or the number of carbons designated ($C_1$-$C_{10}$ means 1 to 10 carbons). Exemplary alkyl groups include methyl, ethyl, n-propyl, isopropyl, n-butyl, sec-butyl, isobutyl, tert-butyl, n-pentyl, n-hexyl, isohexyl, n-heptyl, 4,4-dimethylpentyl, n-octyl, 2,2,4-trimethylpentyl, nonyl, decyl and the like.

The term "optionally substituted alkyl" as used herein by itself or part of another group refers to an alkyl as defined above that is optionally substituted with one to three substituents independently selected from nitro, cyano, amino, optionally substituted cycloalkyl, optionally substituted heteroaryl, optionally substituted heterocycle, alkoxy, aryloxy, arylalkyloxy, alkylthio, carboxamido, sulfonamido, —COR, —SO$_2$R, —N(R)COR, —N(R)SO$_2$R or —N(R)C=N(R)-amino, wherein R may be an alkyl group. Exemplary substituted alkyl groups include —CH$_2$OCH$_3$, —CH$_2$CH$_2$NH$_2$, —CH$_2$CH$_2$CN, —CH$_2$SO$_2$CH$_3$ and the like.

The compounds of the present invention may form salts which are also within the scope of this invention. Reference to a compound of the present invention herein is understood to include reference to salts thereof, unless otherwise indicated. The term "salt(s)" as used herein denotes acidic and/or basic salts formed with inorganic and/or organic acids and bases. In addition, when a compound of the present invention contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound with an amount of acid or base, such as an equivalent amount, in a medium such as one in which the salt precipitates or in an aqueous medium followed by lyophilization.

The compounds of the present invention which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrobromic acid), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of the present invention which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

The stereochemical terms and conventions used in the specification are consistent with those described in *Pure & Appl. Chem.* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The term "asymmetric carbon atom" refers to a carbon atom in a molecule of an organic compound that is attached to four different atoms or groups of atoms.

The term "predominantly" means in a ratio greater than 50:50.

The term "leaving group" or "LG" refers to an atom or group that becomes detached from an atom or group in what is considered to be the residual or main part of the substrate in a specified reaction. In amide coupling reactions, exemplary leaving groups include —F, —Cl, —Br, —OC$_6$F$_5$ and the like.

The term "isolated" for the purposes of the present invention designates a material (e.g. a chemical compound) that has been removed from its original environment (the environment in which it is naturally present).

Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the active compound is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

Suitable formulations for parenteral administration include aqueous solutions of the ligand in water-soluble form, for example, water-soluble salts and alkaline solutions. In addition, suspensions of the active agent as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

Examples of antioxidants which may be added to the pharmaceutical compositions include BHA and BHT.

Pharmaceutical compositions may contain from 0.01% to 99% by weight of the active agent. Compositions may be either in single or multiple dose forms. The amount of ligand in any particular pharmaceutical composition will depend upon the effective dose, that is, the dose required to elicit the desired gene expression or suppression Suitable routes of administering the pharmaceutical compositions include oral, buccal, sublingual, parenteral (including subcutaneous, intramuscular, intravenous, and by nasogastric tube). It will be understood by those skilled in the art that the preferred route of administration will depend upon the condition being treated and may vary with factors such as the condition of the recipient. The pharmaceutical compositions may be administered one or more times daily.

EXAMPLES OF GENERAL SYNTHETIC METHODS

Synthesis of Aminoacyl-phenazopyridine (PAP) Derivatives

Example 1

Preparation of Boc-glycyl-phenazopyridine

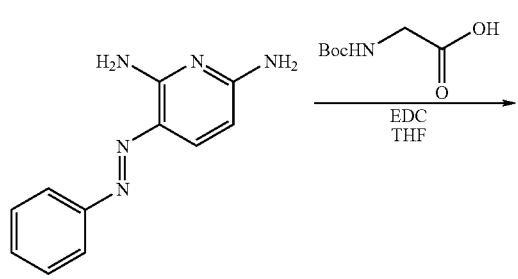

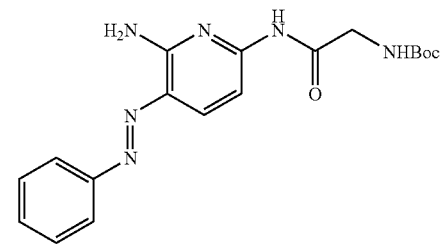

To a solution of 875 mg (5 mmol) of Boc-glycine in 15 mL of THF was added 955 mg (5 mmol) of 1-(3-dimethylaminopropyl)-3-ethylcarbodiimide hydrochloride followed by 1.06 g (5 mmol) of phenazopyridine. The reaction mixture was stirred for 22 h at room temperature at which point an additional 875 mg (5 mmol) of Boc-glycine and 955 mg (5 mmol) of 1-(3-dimethylaminopropyl)-3-ethyl carbodiimide hydrochloride were added. After stirring for an additional 48 h, the precipitated solid was filtered and the filtrate was concentrated to dryness. The residue was dissolved in 40 mL of ethyl acetate and washed with two 40-mL portions of saturated aqueous sodium bicarbonate. The organic layer was dried over sodium sulfate, filtered and the filtrate was concentrated under diminished pressure to give 2.24 g of the crude product as an orange oil. The product was purified by column chromatography on 62 g of silica gel using 50:50 hexane-ethyl acetate as the eluant. Boc-glycyl-phenazopyridine was obtained as an orange oil: yield 330 mg (18%); $^1$H NMR (CDCl$_3$) δ 1.58 (s, 9H), 4.00 (d, 2H, J=4 Hz), 7.47 (m, 4H), 7.80 (m, 2H), 8.17 (d, 1H, J=9 Hz) and 8.29 (br s, 1H). Anal. Calcd for C$_{18}$H$_{22}$N$_6$O$_3$.0.25 H$_2$O: C, 57.67; H, 6.05; N, 22.42. Found: C, 57.86; H, 6.01; N, 22.42.

Example 2

Preparation of Glycyl-phenazopyridine (6-N-Glycylphenazopyridine)

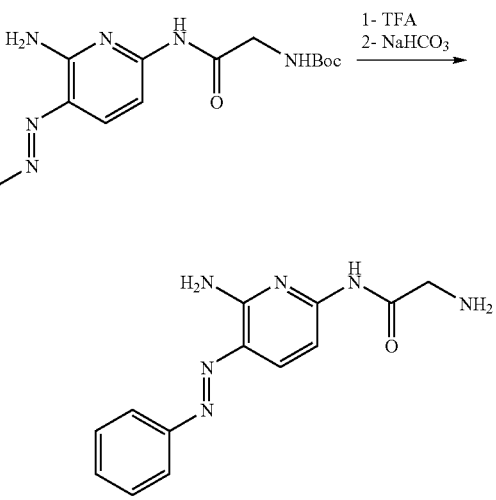

To a solution of 330 mg (0.89 mmol) of Boc-glycyl-phenazopyridine in 20 mL of dichloromethane was added 3.10 mL (41.3 mmol) of trifluoroacetic acid. The reaction mixture was stirred at room temperature for 2.5 h at which point the reaction was complete. The reaction mixture was poured into 40 mL of saturated aqueous sodium bicarbonate solution, the layers were separated and the organic layer was washed once with 40 mL of saturated sodium bicarbonate solution. After drying over sodium sulfate, filtration and removal of the solvent under diminished pressure, glycyl-phenazopyridine was obtained as an orange solid: yield 140 mg (58%); $^1$H NMR (CDCl$_3$) δ 3.5 (s, 2H), 7.4-7.6 (m, 3H), 7.75-7.8 (m, 3H) and 8.2 (d, 1H); mass spectrum (ESI), m/z 271 (M+H)$^+$ and 293 (M+Na)$^+$. Anal. calcd for C$_{13}$H$_{14}$N$_6$O.0.50 H$_2$O: C, 55.90; H, 5.41; N, 30.09. Found: C, 56.13; H, 5.16; N, 29.87.

Example 3

Preparation of Glycyl-phenazopyridine Hydrochloride Salt

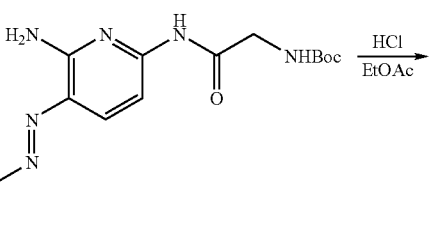

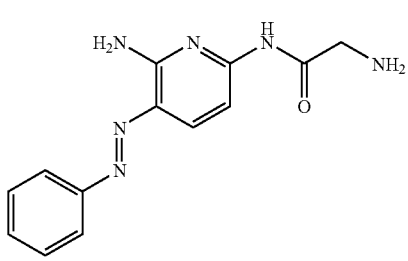

To a cooled (0-5° C.) solution of 1.0 g (2.70 mmol) of Boc-glycyl-phenazopyridine in 20 mL of EtOAc was bubbled slowly dry HCl (g) [prepared by adding a 36% solution of HCl (5 mL) to $H_2SO_4$]. The reaction mixture was stirred at room temperature for 3 h following which HPLC analysis showed that the reaction was complete. The thick mixture was filtered and the product was washed with four 15-mL portions of EtOAc and dried under diminished pressure over $P_2O_5$ at 45° C. for 6 h. Glycyl-phenazopyridine dihydrochloride was obtained as an orange solid: yield 878 mg (94%); $^1$H NMR (DMSO-$d_6$) δ 3.88 (s, 2H), 7.51 (m, 4H), 7.89 (d, 2H, J=7.2 Hz), 8.09 (d, 1H, J=8.7 Hz), 8.46 (m, 3H) and 11.10 (s, 1H). Anal. calcd for $C_{13}H_{16}Cl_2N_6O.0.80\ H_2O$: C, 43.66; H, 4.96; N, 23.50; Cl, 19.83. Found: C, 43.96; H, 4.64; N, 23.60; Cl, 20.10.

Example 4

Preparation of Glycyl-phenazopyridine Mesylate Salt

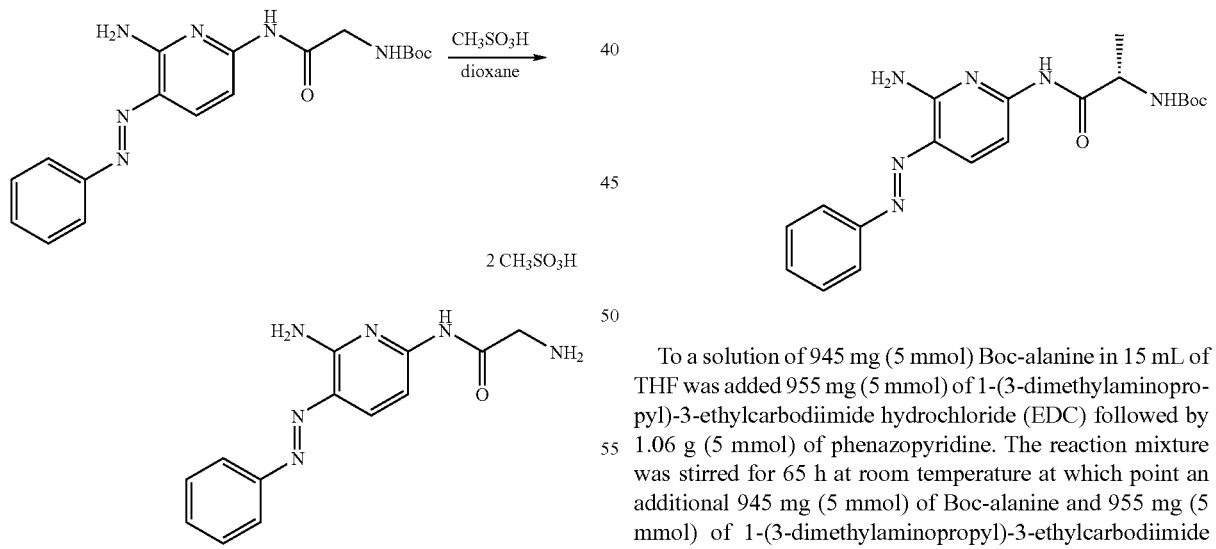

To a solution of 300 mg (0.8 mmol) of Boc-glycyl-phenazopyridine in 8 mL of dioxane was added dropwise 207 μL (3.2 mmol) of methanesulfonic acid. The reaction mixture was stirred at room temperature for 90 min after which only 4% conversion was observed. After 1 h 45 min, another 414 μL (6.4 mmol) of methanesulfonic acid were added and stirring was continued at room temperature for 3 h. The precipitated product was filtered, washed with three 6-mL portions of 1,4-dioxane and three 6-mL portions of acetone and dried under vacuum at 45° C. over $P_2O_5$ for 18 h. Glycyl-phenazopyridine mesylate salt was obtained as an orange solid: yield 352 mg (94%); $^1$H NMR (DMSO-$d_6$) δ 2.41 (s, 6H), 3.89 (s, 2H), 7.43-7.56 (m, 4H), 7.89 (d, 2H, J=7.5 Hz), 8.10 (m, 4H) and 10.87 (s, 1H). Anal. calcd for $C_{13}H_{14}N_6O.2.65\ CH_3SO_3H$: C, 35.81; H, 4.72; N, 16.01; S, 16.19. Found: C, 35.47; H, 4.79; N, 15.82; S, 15.85.

Example 5

Preparation of Boc-alanyl-phenazopyridine

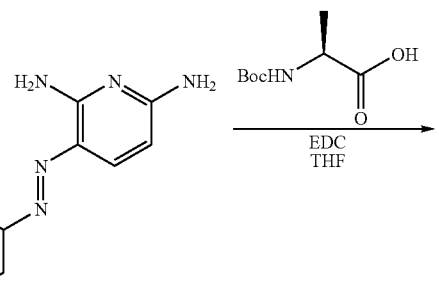

To a solution of 945 mg (5 mmol) Boc-alanine in 15 mL of THF was added 955 mg (5 mmol) of 1-(3-dimethylaminopropyl)-3-ethylcarbodiimide hydrochloride (EDC) followed by 1.06 g (5 mmol) of phenazopyridine. The reaction mixture was stirred for 65 h at room temperature at which point an additional 945 mg (5 mmol) of Boc-alanine and 955 mg (5 mmol) of 1-(3-dimethylaminopropyl)-3-ethylcarbodiimide hydrochloride were added. After stirring for an additional 24 h, the reaction mixture was concentrated to dryness, dissolved in 40 mL of ethyl acetate and extracted with two 40-mL portions of saturated aqueous sodium bicarbonate solution. The organic layer was dried over sodium sulfate and filtered. The filtrate was concentrated under diminished pressure to give 2.1 g of an orange oil. The oil was purified by column chromatography on 60 g of silica gel using 50:50 hexane-ethyl acetate as the eluant. Boc-alanyl-phenazopyridine was obtained as an orange oil: yield 610 mg (32%).

Example 6

Preparation of Alanyl-phenazopyridine

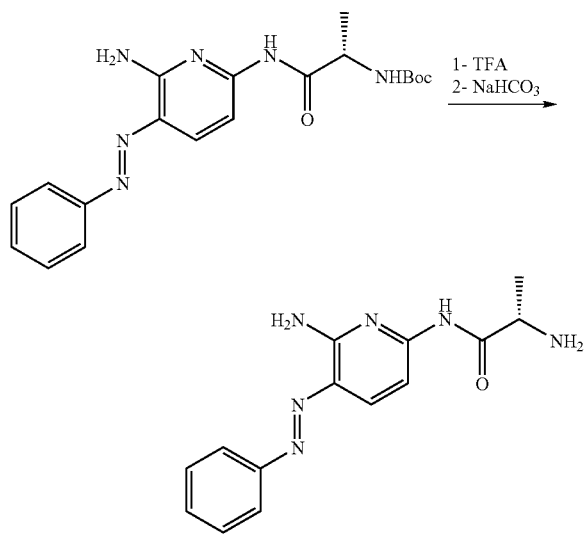

To a solution of 610 mg (1.59 mmol) of Boc-alanyl-phenazopyridine in 15 mL of dichloromethane was added 5.51 mL (73.6 mmol) of trifluoroacetic acid. The reaction mixture was stirred at room temperature for 3 h at which point the reaction was complete. The reaction mixture was poured into 40 mL of saturated aqueous sodium bicarbonate solution, the layers were separated and the organic layer was washed once with 40 mL of saturated aqueous sodium bicarbonate. The organic layer was dried over sodium sulfate, filtered and the filtrate was concentrated under diminished pressure. Alanyl-phenazopyridine was obtained as an orange solid: yield 290 mg (64%); $^1$H NMR (DMSO-$d_6$) δ 1.3 (d, 3H), 3.6 (q, 1H), 7.4-7.7 (m, 4H), 7.9-8.0 (m, 2H) and 8.1 (d, 1H); mass spectrum (ESI), m/z 285 (M+H)$^+$ and 307 (M+Na)$^+$.

Example 7

Preparation of Boc-methionyl-phenazopyridine

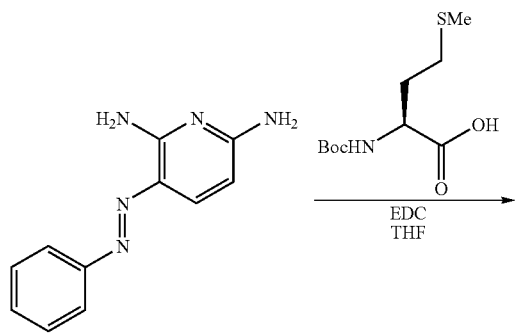

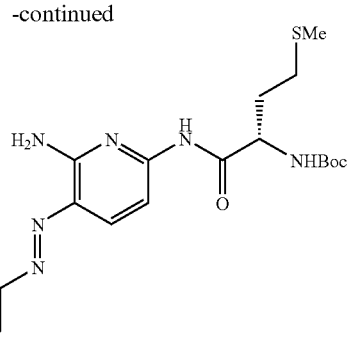

To a solution of 1.24 g (5 mmol) of Boc-methionine in 10 mL of THF was added 955 mg (5 mmol) of 1-(3-dimethylaminopropyl)-3-ethylcarbodiimide hydrochloride (EDC) followed by 1.06 g (5 mmol) of phenazopyridine. The reaction mixture was stirred at room temperature for 24 h at which point an additional 1.24 g (5 mmol) of Boc-methionine and 955 mg (5 mmol) of 1-(3-dimethylaminopropyl)-3-ethylcarbodiimide hydrochloride were added. After stirring for an additional 48 h, the reaction mixture was concentrated to dryness, dissolved in 40 mL of ethyl acetate and extracted with two 40 mL portions of saturated aqueous sodium bicarbonate solution. The organic layer was dried over sodium sulfate, filtered and the filtrate was concentrated under diminished pressure. The crude orange oil was purified by column chromatography on 32 g of silica gel using 50:50 hexane-ethyl acetate as the eluant. Boc-methionyl-phenazopyridine was obtained as an orange oil: yield 700 mg (32%).

Example 8

Preparation of Methionyl-phenazopyridine

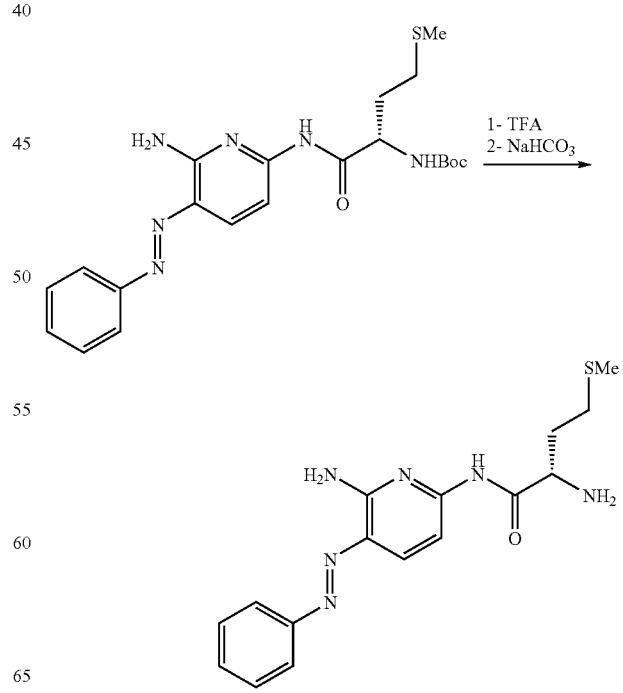

To a solution of 700 mg (1.57 mmol) of Boc-methionyl-phenazopyridine in 15 mL of dichloromethane was added 2.3 mL (31.4 mmol) of trifluoroacetic acid. The reaction mixture was stirred at room temperature for 2 h at which point the reaction was complete. The reaction mixture was poured into 60 mL of saturated aqueous sodium bicarbonate solution, the layers were separated and the organic layer was washed with 40 mL of saturated aqueous sodium bicarbonate solution. The organic layer was dried over sodium sulfate, filtered and the filtrate was concentrated under diminished pressure. Methionyl-phenazopyridine was obtained as an orange solid: yield 247 mg (46%); $^1$H NMR (CDCl$_3$) δ 1.8-1.9 (m, 1H), 2.1 (s, 3H), 2.2-2.4 (m, 1H), 2.6-2.8 (m, 2H), 3.7 (m, 1H), 7.4-7.6 (m, 3H), 7.8-7.9 (m, 3H) and 8.2 (d, 1H); mass spectrum (ESI), m/z 345 (M+H)$^+$ and 367 (M+Na)$^+$.

Example 9

Preparation of bis-Boc-tryptophanyl-phenazopyridine

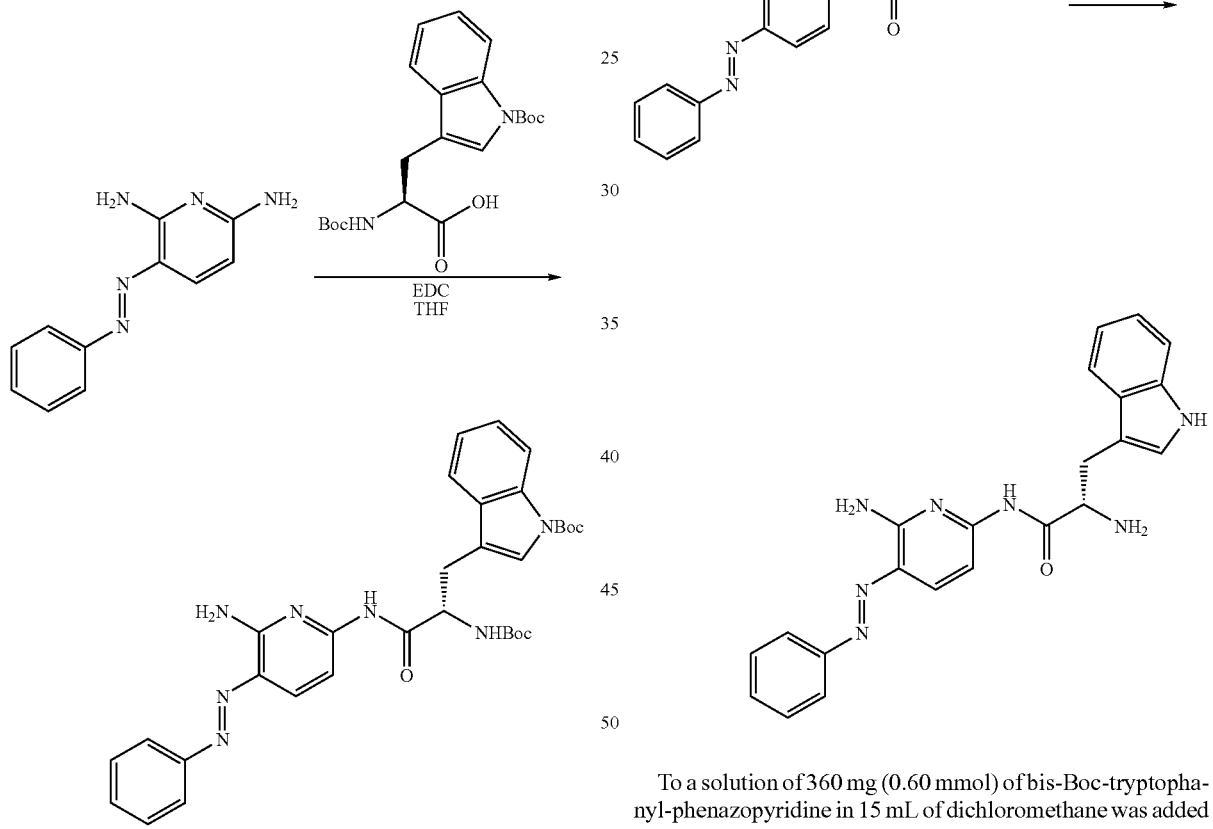

To a solution of 2.0 g (5 mmol) of bis-Boc-tryptophan in 15 mL of THF was added 955 mg (5 mmol) of 1-(3-dimethylaminopropyl)-3-ethylcarbodiimide hydrochloride (EDC) followed by 1.06 g (5 mmol) of phenazopyridine. The reaction mixture was stirred for 6 h at room temperature at which point an additional 2.0 g (5 mmol) of bis-Boc-tryptophan and 955 mg (5 mmol) of 1-(3-dimethylaminopropyl)-3-ethyl carbodiimide hydrochloride were added. After stirring for an additional 72 h, the reaction mixture was filtered and the filtrate was concentrated under diminished pressure. The residue was dissolved in 40 mL of ethyl acetate and extracted with two 40-mL portions of saturated aqueous sodium bicarbonate. The organic layer was dried over sodium sulfate, filtered and the filtrate was concentrated under diminished pressure to give 5.47 g of an orange foam. The crude product was purified by column chromatography on 41 g of silica gel using 50:50 hexane-ethyl acetate as the eluant. Bis-Boc-tryptophanyl-phenazopyridine was obtained as an orange solid: yield 2.43 g (81%).

Example 10

Preparation of Tryptophanyl-phenazopyridine

To a solution of 360 mg (0.60 mmol) of bis-Boc-tryptophanyl-phenazopyridine in 15 mL of dichloromethane was added 1.80 mL (24.0 mmol) of trifluoroacetic acid. The reaction mixture was stirred at room temperature for 1.5 h at which point the reaction was complete. The reaction mixture was poured into 50 mL of saturated aqueous sodium bicarbonate solution, the layers were separated and the organic layer was washed once with 40 mL of saturated aqueous sodium bicarbonate solution. The organic layer was dried over sodium sulfate, filtered and the filtrate was concentrated under diminished pressure. The crude product was purified by chromatography on 41 g of silica gel using 50:50 hexane-ethyl acetate as eluent. Tryptophanyl-phenazopyridine was obtained as an orange solid: yield 10 mg (4%); $^1$H NMR (CDCl$_3$) δ 3.0-3.2 (m, 1H), 3.4-3.6 (m, 1H), 3.8-4.0 (m, 1H), 7.0-7.3 (m, 4H), 7.4-7.6 (m, 4H), 7.8-8.0 (m, 2H), 8.2 (d, 1H) and 10.0 (br s, 1H); mass spectrum (ESI) m/z 400 (M+H)$^+$ and 422 (M+Na)$^+$.

Example 11

Preparation of Boc-valyl-phenazopyridine

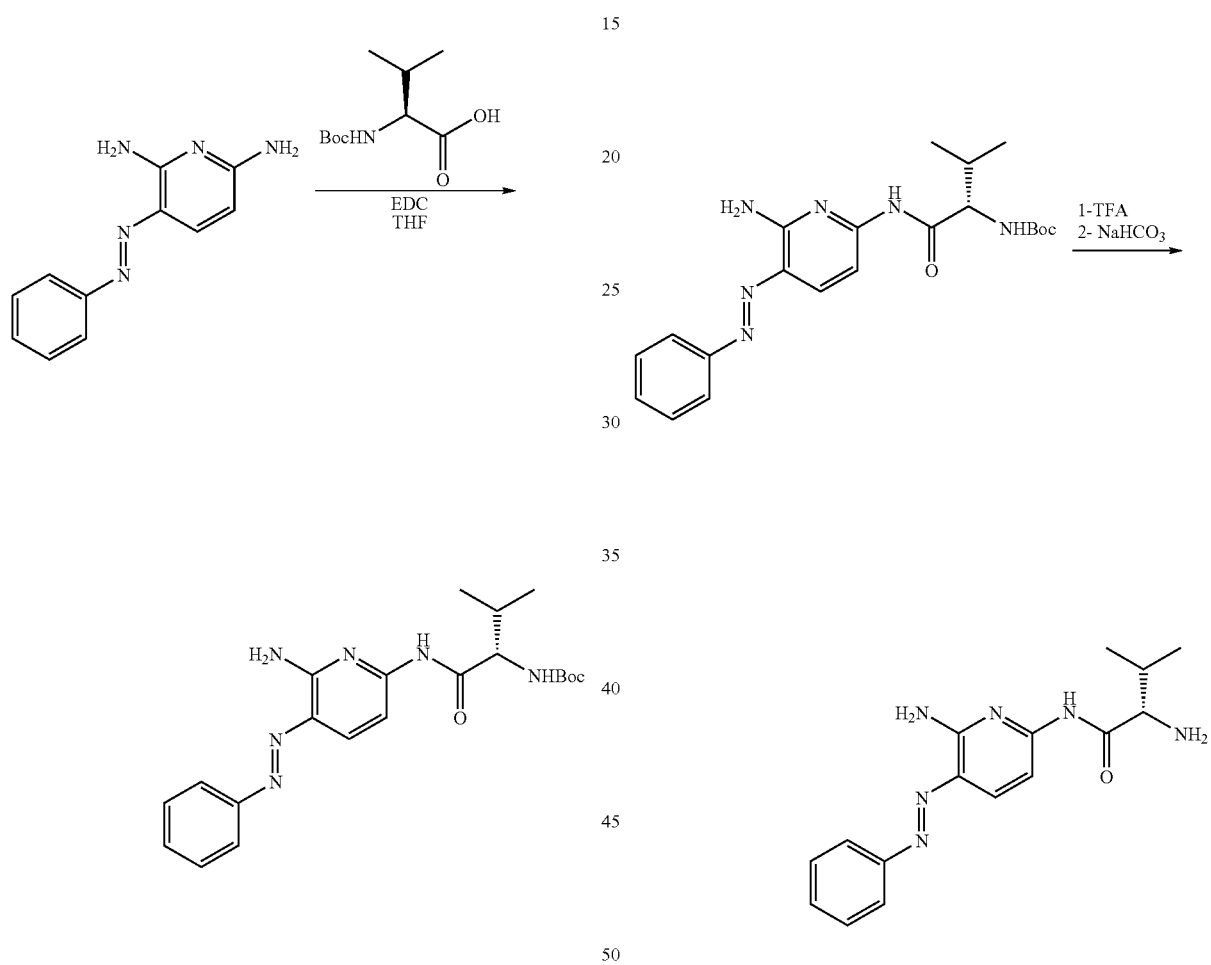

To a solution of 1.51 g (7.0 mmol) of Boc-valine in 10 mL of THF was added 1.33 g (7.0 mmol) of 1-(3-dimethylaminopropyl)-3-ethylcarbodiimide hydrochloride (EDC) followed by 1.5 g (7.0 mmol) of phenazopyridine. The reaction mixture was stirred at room temperature for 24 h at which point an additional 1.51 g (7.0 mmol) of Boc-valine, 1.33 g (7.0 mmol) of 1-(3-dimethylaminopropyl)-3-ethyl carbodiimide hydrochloride and 1.4 g (14 mmol) of N-methylmorpholine were added, and the mixture was stirred for an additional 24 h. The solvent was concentrated under diminished pressure and the residue was dissolved in ethyl acetate and washed two times with saturated aqueous sodium bicarbonate solution. The organic layer was dried over sodium sulfate, filtered and the filtrate was concentrated under diminished pressure. The crude product was purified by column chromatography on silica gel eluting with 1:1 hexanes-ethyl acetate to give Boc-valyl-phenazopyridine as an orange oil: yield 300 mg (10%).

Example 12

Preparation of Valyl-phenazopyridine

To a solution of 300 mg (0.73 mmol) of Boc-valyl-phenazopyridine in 10 mL of dichloromethane was added 1.72 g (1.1 mL, 14.6 mmol) of trifluoroacetic acid. The reaction mixture was stirred at room temperature for 3.5 h, then was added dropwise to a saturated aqueous sodium bicarbonate solution. The layers were separated and the aqueous layer was extracted once with dichloromethane. The combined organic layer was dried over sodium sulfate, filtered and the filtrate concentrated under diminished pressure. Valyl-phenazopyridine was obtained as an orange solid: yield 110 mg (48%); $^1$H NMR (CDCl$_3$) δ 0.95 (d, 3H), 1.05 (d, 3H), 2.4

(m, 1H), 3.4 (s, 1H), 7.4-7.6 (m, 3H), 7.7-7.9 (m, 3H) and 8.1 (d, 1H); mass spectrum (ESI), m/z 313 (M+H)+ and 335 (M+Na)+.

Example 13

Preparation of bis-Boc-lysyl-phenazopyridine

Example 14

Preparation of Lysyl-phenazopyridine

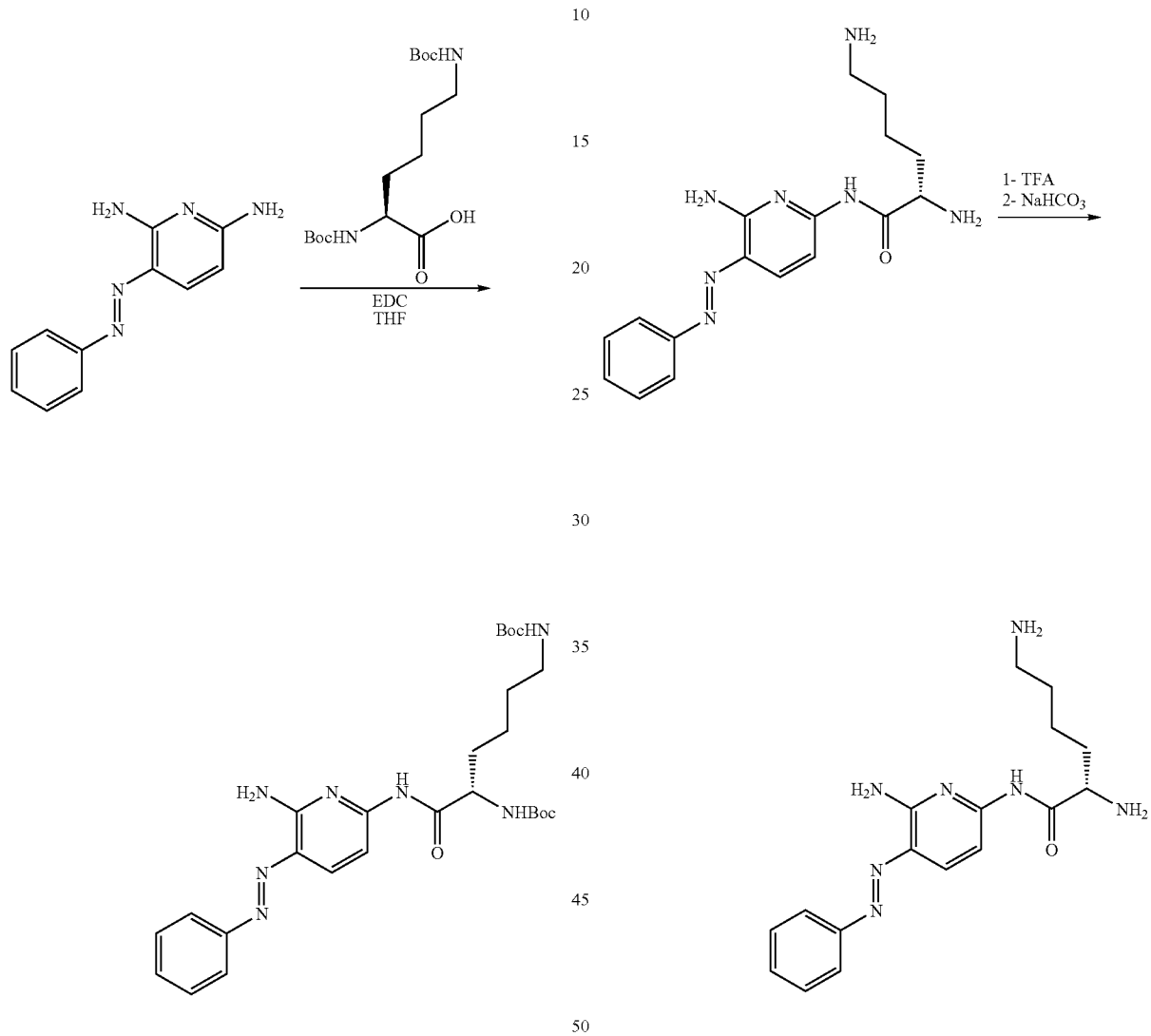

To a solution of 1.73 g (5 mmol) of bis-Boc-lysine in 10 mL of THF was added 955 mg (5 mmol) of 1-(3-dimethylaminopropyl)-3-ethyl carbodiimide hydrochloride (EDC) followed by 1.06 g (5 mmol) of phenazopyridine. The reaction mixture was stirred at room temperature for 24 h. The solvent was removed under diminished pressure and the residue was dissolved in ethyl acetate and washed twice with saturated aqueous sodium bicarbonate solution. The organic layer was dried over sodium sulfate, filtered and the filtrate was concentrated under diminished pressure to give the crude product as a red oil. Purification of the crude product on a silica gel column, eluting with 1:1 hexanes-ethyl acetate, gave bis-Boc-lysyl-PAP as an orange oil: yield 360 mg (13%).

To a solution of 360 mg (0.66 mmol) of bis-Boc-lysyl-phenazopyridine in 20 mL of dichloromethane was added 3.40 g (2.2 mL, 29.7 mmol) of trifluoroacetic acid. The reaction mixture was stirred at room temperature for 22 h. An additional 1.53 g (13.4 mmol) of trifluoroacetic acid was added and stirring was continued at room temperature for 2 h. The reaction mixture was added to saturated aqueous sodium bicarbonate solution, causing an orange solid to precipitate. The product was filtered, washed twice with heptane and isopropanol, and dried under diminished pressure at room temperature: yield 200 mg (88%); $^1$H NMR (CD$_3$OD) δ 1.5-

2.2 (m, 6H), 2.9 (t, 2H), 3.7 (t, 1H), 7.5-7.7 (m, 4H), 8.0 (m, 2H) and 8.3 (d, 1H); mass spectrum (ESI), m/z 342 (M+H)+ and 364 (M+Na)+.

Example 15

Preparation of Boc-(N-tosyl-histidinyl)-phenazopyridine

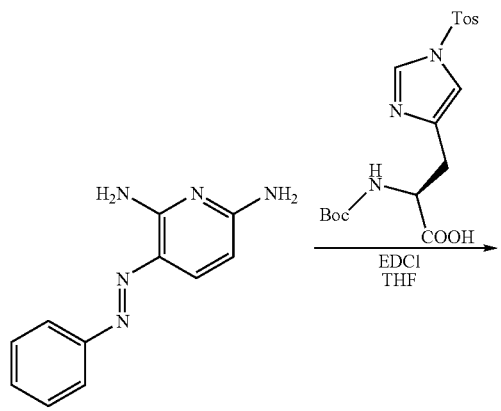

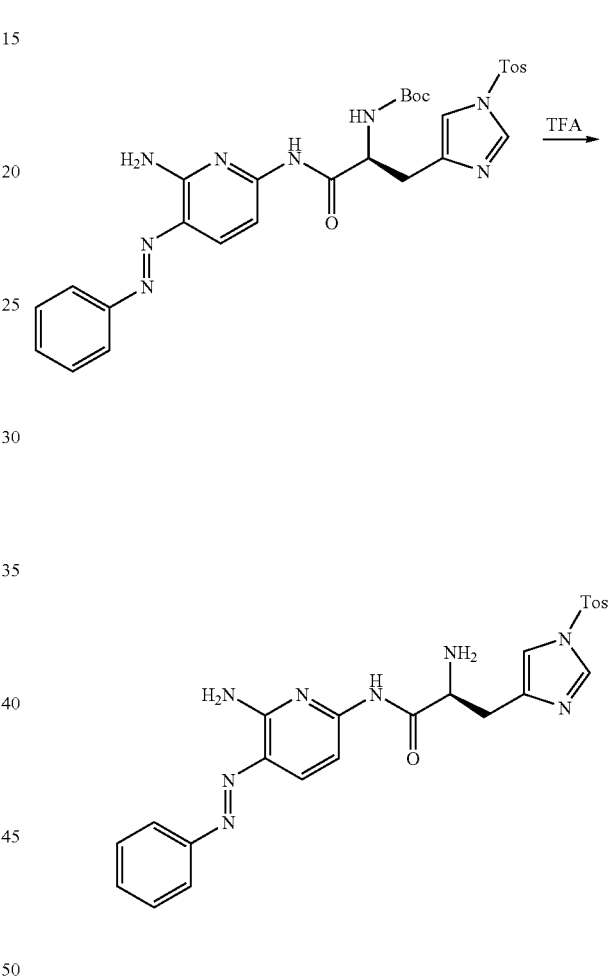

A sample of 1.40 g (7.33 mmol) of EDCI was added in one portion to a solution of 3.00 g (7.33 mmol) of Boc-his(Tos)-OH in 60 mL of anhydrous THF. The reaction mixture was stirred at room temperature for 30 min, then 1.56 g (7.33 mmol) of phenazopyridine was added in one portion. The reaction mixture was stirred at room temperature for 96 h (until no further reaction progress was detected by HPLC). The solvent was concentrated under diminished pressure and the residue was dissolved in 200 mL of EtOAc, washed successively with 150 mL of water, 150 mL of satd. aq. NaHCO$_3$ solution, 150 mL of brine, and dried (Na$_2$SO$_4$). The solvent was concentrated under diminished pressure. To remove unreacted phenazopyridine, the oily residue was purified by chromatography on an alumina oxide column (elution with CHCl$_3$, then 99:1 CHCl$_3$-MeOH). Further purification on a silica gel column (elution with 99:1 CHCl$_3$-MeOH, then 98:2 CHCl$_3$-MeOH) afforded the product as an orange solid: yield 0.43 g (10%).

Example 16

Preparation of N-Tosyl-histidinyl-phenazopyridine

A sample of 1.28 mL (17.2 mmol) of trifluoroacetic acid was added dropwise to a solution of 0.26 g (0.43 mmol) of Boc-(N-tosylhistidinyl)-phenazopyridine in 12 mL of anhydrous CH$_2$Cl$_2$. The reaction mixture was stirred at room temperature for 3 h, and then added to a saturated aqueous solution of NaHCO$_3$. The organic layer was separated and dried (Na$_2$SO$_4$). The solvent was concentrated under diminished pressure to give the crude product as an orange solid: yield 200 mg (100%). A pure sample was obtained using preparative HPLC (93% yield); elution was with 0.1% HOAc in a gradient of CH$_3$CN; mass spectrum (ESI) m/z 505 (M+H)+ and 527 (M+Na)+. Anal. calcd for $C_{24}H_{24}O_3S \cdot HOAc$: C, 55.31; H, 5.00; N, 19.85. Found: C, 55.71; H, 4.78; N, 19.57.

Example 17

Preparation of Histidinyl-phenazopyridine

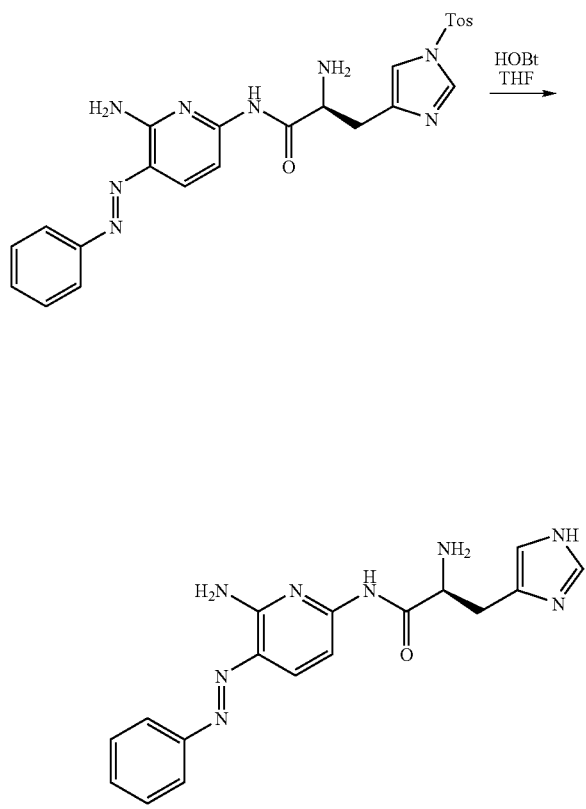

A sample of 65 mg (0.48 mmol) of 1-hydroxybenzotriazole was added to a suspension of 12 mg (0.24 mmol) of N-tosyl-histidinyl-phenazopyridine (0.12 g, 0.24 mmol) in 10 mL of anhydrous THF. The reaction mixture was stirred at room temperature for 2 h before an additional 65 mg (0.48 mmol) portion of 1-hydroxybenzotriazole was added and the mixture was stirred for an additional 3 h. The solvent was concentrated under diminished pressure and the residue was dissolved in 15 mL of EtOAc and extracted with two 10-mL portions of 0.05 N HCl. The combined aqueous layer was adjusted to pH~8 by the addition of a saturated aqueous solution of $Na_2CO_3$ and then extracted with three 15-mL portions of EtOAc. The combined organic layer was dried ($Na_2SO_4$) and the solvent was concentrated under diminished pressure to give an orange solid. It was purified by preparative HPLC to give the product as a dark orange solid: yield 40 mg (41%); $^1$H NMR (500 MHz, DMSO-$d_6$) δ 1.86 (s, 6H), 3.19-3.31 (m, 2H), 4.39 (br s, 1H), 7.46-7.53 (m, 6H), 7.88 (d, 2H), 8.07 (d, 1H), 8.45 (br s, 4H) and 9.03 (s, 1H); mass spectrum (ESI) m/z 373 (M+Na+); mass spectrum (ESI) m/z 373 (M+Na)+.

Synthesis of Phenazopyridine (PAP) Carbamates

Example 18

Preparation of Ethylcarbamyl-phenazopyridine

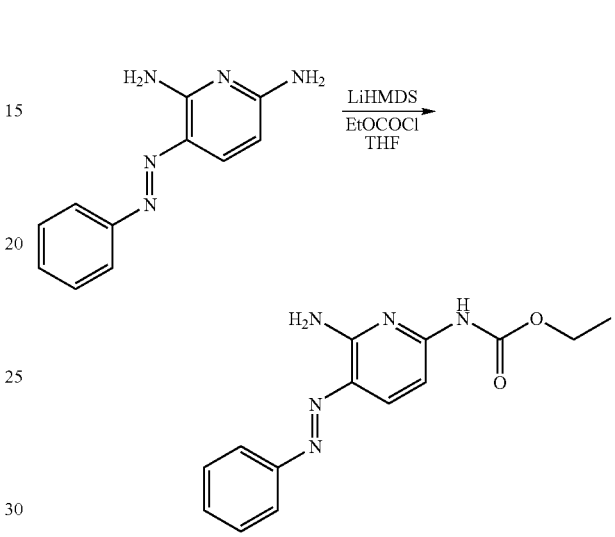

A solution of 4.68 mL (4.68 mmol) of lithium hexamethyldisilazide (LiHMDS) (1M in THF) was added dropwise, over a period of 10 min at room temperature, to a solution of 0.50 g (2.34 mmol) of phenazopyridine in 10 mL of THF. After an additional 10 min, a solution of 0.26 g (0.23 mL, 2.40 mmol) of ethyl chloroformate in 5 mL of THF was added dropwise to the reaction mixture over a period of 5 min. The reaction mixture was stirred at room temperature for 1 h. The solvent was concentrated under diminished pressure and the residue was purified on a silica gel column (17×3 cm). Elution with a stepwise gradient of dichloromethane in hexane (20→80%) gave the monocarbamate as an orange solid: yield 203 mg (30%); $^1$H NMR (CD$_3$OD) δ 1.32 (t, 3H, J=7.0 Hz), 4.22 (q, 2H, J=7.0, 14.2 Hz), 7.33 (d, 1H, J=9.0 Hz), 7.40 (m, 1H), 7.48 (t, 2H, J=7.2 Hz), 7.82 (d, 2H, J=9.9 Hz) and 8.06 (d, 1H, J=9.0 Hz); mass spectrum (ESI) m/z 286 (M+H)+ and 308 (M+Na)+.

Example 19

Preparation of Benzylcarbamyl-phenazopyridine

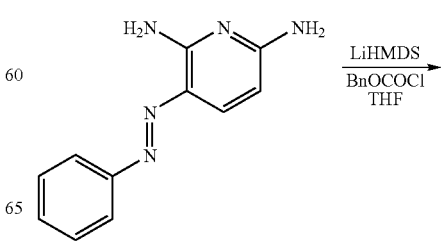

-continued

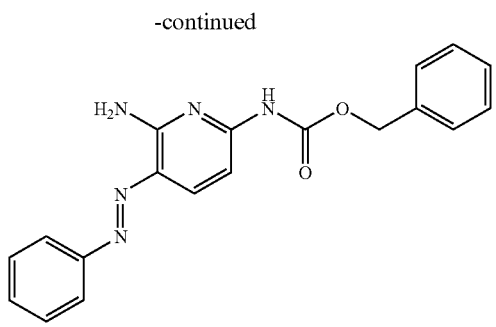

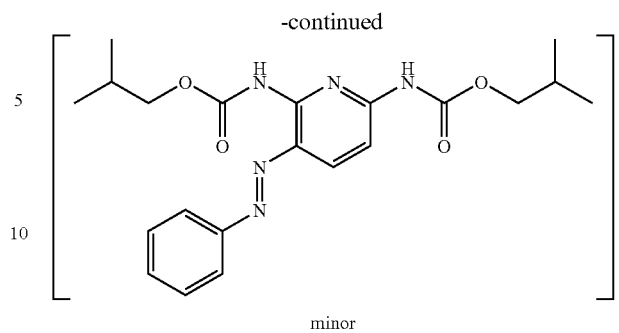

minor

A solution of 4.68 mL (4.68 mmol) of lithium hexamethyldisilazide (LiHMDS) (1M in THF) was added dropwise, over a period of 10 min at room temperature, to a solution of 0.5 g (2.34 mmol) of phenazopyridine in 10 mL of THF. After an additional 10 min, a solution of 0.41 g (0.34 mL, 2.40 mmol) of benzyl chloroformate in 5 mL of THF was added dropwise to the reaction mixture over a period of 5 min. The reaction mixture was stirred at room temperature for 1 h. The solvent was concentrated under diminished pressure and the residue was purified on a silica gel column (18×3 cm). Elution with a stepwise gradient of dichloromethane in hexane (50→80%), then 1% $Et_3N$ in dichloromethane gave the monocarbamate as an orange solid: yield 273 mg (33%); $^1$H NMR ($CD_3OD$) δ 5.21 (s, 2H), 7.32-7.50 (m, 9H), 7.81 (d, 2H, J=9.0 Hz) and 8.06 (d, 1H, J=8.7 Hz); mass spectrum (ESI) m/z 348 $(M+H)^+$ and 370 $(M+Na^+)^+$.

A solution of 4.68 mL (4.68 mmol) of lithium hexamethyldisilazide LiHMDS (1M in THF) was added dropwise, over a period of 10 min at room temperature, to a solution of 0.5 g (2.34 mmol) of phenazopyridine in 10 mL of THF. After an additional 10 min., a solution of 0.32 g (0.31 mL, 2.40 mmol) of isobutyl chloroformate in 5 mL of THF was added dropwise to the reaction mixture over a period of 5 min. The reaction mixture was stirred at room temperature for 18 h. The solvent was concentrated under diminished pressure and the residue purified on a silica gel column (17×3 cm). Elution with a stepwise gradient of EtOAc in hexane (0 to 15%) gave the bis-carbamate as an orange solid: yield 140 mg (14%), followed by the monocarbamate as an orange solid: yield 202 mg (27%); $^1$H NMR (DMSO-$d_6$) δ 0.93 (d, 6H, J=6.9 Hz), 1.92 (m, 1H), 3.89 (d, 2H, J=6.6 Hz), 7.31 (d, 1H, J=8.7 Hz), 7.44 (m, 1H), 7.52 (t, 2H, J=8.7 Hz), 7.86 (d, 2H, J=8.1 Hz) and 8.02 (d, 1H, J=8.7 Hz); mass spectrum (ESI) m/z 314 $(M+H)^+$ and 336 $(M+Na)^+$.

Example 20

Preparation of Isobutylcarbamyl-phenazopyridine

Example 21

Preparation of Dodecylcarbamyl-phenazopyridine

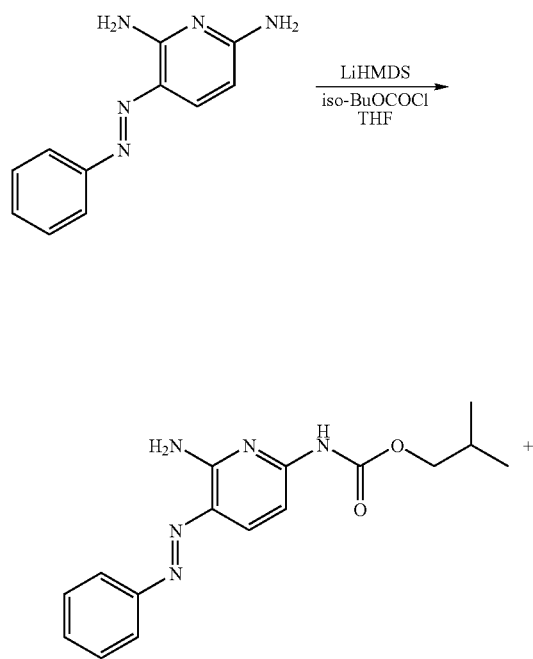

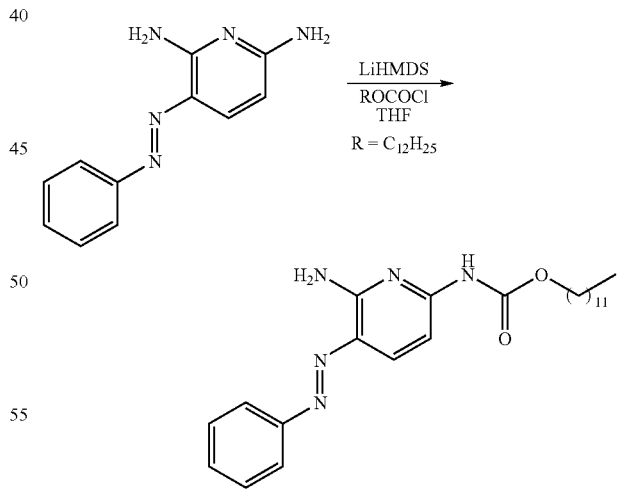

A solution of 4.68 mL (4.68 mmol) of lithium hexamethyldisilazide LiHMDS (1M in THF) was added dropwise, over a period of 10 min at room temperature, to a solution of 0.5 g (2.34 mmol) of phenazopyridine in 10 mL of THF. After an additional 10 min at −5° C., a solution of 0.59 g (0.65 mL, 2.40 mmol) of dodecyl chloroformate in 5 mL of THF (5 mL) was added dropwise to the reaction mixture at −5° C. over a period 5 min. The reaction mixture was stirred at −5° C.-0° C.

for 1 h and then at room temperature for 24 h. The solvent was concentrated under diminished pressure and the residue was purified on a silica gel column (18×3 cm). Elution with 20% EtOAc in hexane gave the slightly impure monocarbamate as an orange solid. The product was dissolved in hot EtOAc (5 mL) and the mixture was left to cool to room temperature. The precipitated product was collected by filtration and dried under diminished pressure. The phenazopyridine dodecyl monocarbamate was obtained as an orange solid: yield 361 mg (36%); $^1$H NMR (DMSO-$d_6$) δ 0.83 (t, 3H, J=6.3 Hz), 1.22 (m, 18H), 1.6 (m, 2H), 4.09 (t, 2H, J=6.6 Hz), 7.30 (d, 1H, J=8.7 Hz), 7.43 (m, 1H), 7.51 (t, 2H, J=7.6 Hz), 7.61 (br s, 2H), 7.85 (d, 2H, J=8.4 Hz), 8.01 (d, 1H, J=8.7 Hz) and 10.08 (s, 1H). Anal. calcd for $C_{24}H_{35}N_5O_2 \cdot 1.25\ H_2O$: C, 64.33; H, 8.44; N, 15.63. Found: C, 63.96; H, 7.83; N, 15.44.

Example 22

Preparation of 2-Ethylhexylcarbamyl-phenazopyridine

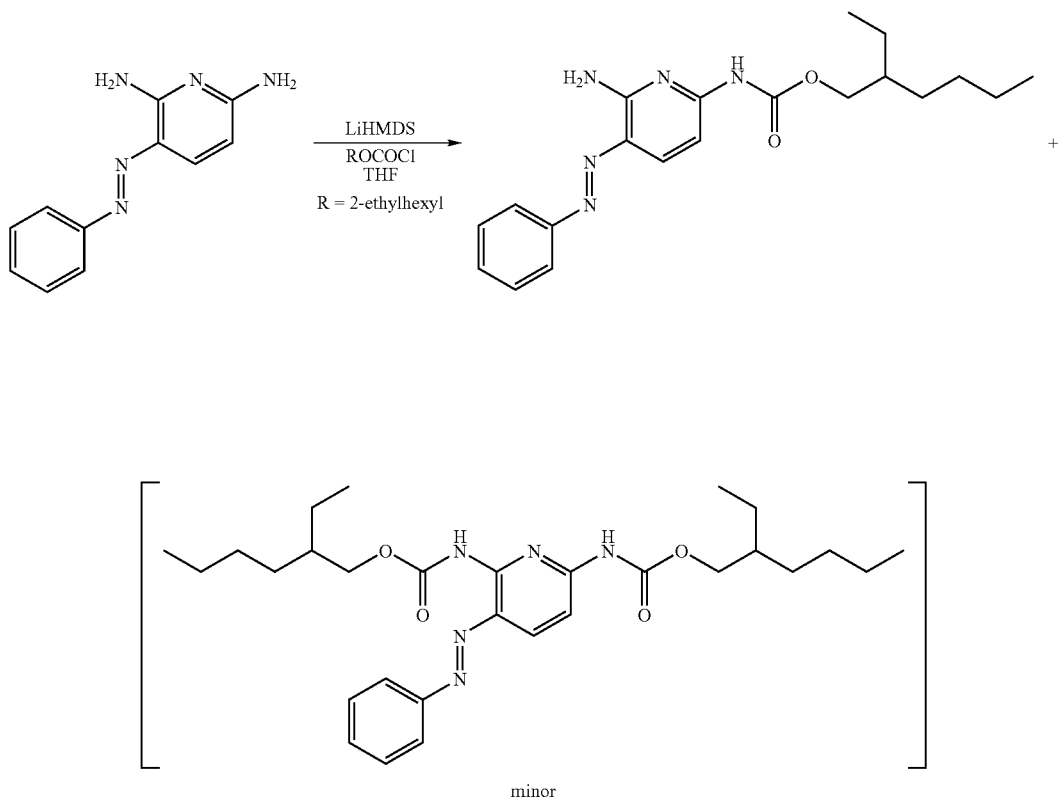

A solution of 2.81 mL (2.81 mmol) of lithium hexamethyldisilazide LiHMDS (1M in THF) was added dropwise, over a period of 13 min at −5° C., to a cooled solution of 0.3 g (1.40 mmol) of phenazopyridine in 10 mL of THF. After an additional 10 min. at −5° C., a solution of 0.28 g (0.28 mL, 1.45 mmol) of 2-ethylhexyl chloroformate in 35 mL of THF was added dropwise at −5° C. over a period of 5 min. The reaction was stirred at 0° C. for 1 h and then at room temperature for 24 h. The solvent was concentrated under diminished pressure and the residue was purified by chromatography on a silica gel column (17×3 cm). Elution with a stepwise gradient of EtOAc in heptanes (0→10%) gave the bis-carbamate as an orange syrup: yield 57 mg (7%), followed by the monocarbamate as an orange syrup: yield 309 mg (59%); $^1$H NMR (DMSO-$d_6$) δ 0.86 (m, 6H), 1.26-1.40 (m, 8H), 1.56 (m, 1H), 4.01 (d, 2H, J=5.7 Hz), 7.31 (d, 1H, J=8.4 Hz), 7.43 (m, 1H), 7.51 (t, 2H, J=7.5 Hz), 7.85 (d, 2H, J=8.1 Hz), 8.01 (d, 1H, J=8.7 Hz) and 10.09 (s, 1H); mass spectrum (ESI) m/z 370 (M+H)$^+$ and 392 (M+Na)$^+$.

Anal. calcd for $C_{20}H_{27}N_5O_2$: C, 65.02; H, 7.37; N, 18.96. Found: C, 65.41; H, 7.43; N, 18.51.

Example 23

Preparation of tert.-Butylcarbamyl-phenazopyridine

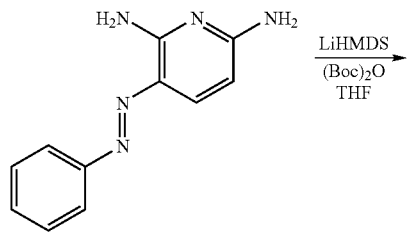

A solution of 4.68 mL (4.68 mmol) of lithium hexamethyldisilazide LiHMDS (1M in THF) was added dropwise, over a period of 8 min at 5° C., to a solution of 0.5 g (2.34 mmol) of phenazopyridine in 10 mL of THF. After an additional 10 min. at −5° C., a solution of 0.53 g (2.46 mmol) of (Boc)$_2$O in 5 mL of THF was added dropwise at 0° C. over a period of 10 min. The reaction mixture was stirred at 0° C. for 1 h and then at room temperature for 2 h. The solvent was concentrated under diminished pressure and the residue was purified on a silica gel column (18×3 cm). Elution with a stepwise gradient of EtOAc in hexanes (0→10%) gave a mixture of the mono and bis-carbamates. The mixture was purified further on a preparative HPLC column. The mono carbamate ($R_t$ 19.9 min.) was obtained as an orange foam: yield 451 mg (61%); $^1$H NMR (DMSO-d$_6$) δ 1.60 (s, 9H), 7.40 (d, 1H, J=9 Hz), 7.56 (m, 1H), 7.63 (t, 2H, J=7.6 Hz), 7.97 (d, 2H, J=8.4 Hz), 8.11 (d, 1H, J=9.0 Hz) and 9.89 (s, 1H); mass spectrum (ESI) m/z 314 (M+H)$^+$ and 336 (M+Na)$^+$. Anal. calcd for $C_{16}H_{19}N_5O_2$: C, 61.33; H, 6.11; N, 22.35. Found: C, 61.37; H, 6.26; N, 22.15. The bis carbamate ($R_t$ 22.5 min.) was obtained as an orange syrup: yield 118 mg (12%); mass spectrum (ESI) m/z 414 (M+H)$^+$ and 436 (M+Na)$^+$.

Example 24

Preparation of Trichloroethylcarbamyl-phenazopyridine

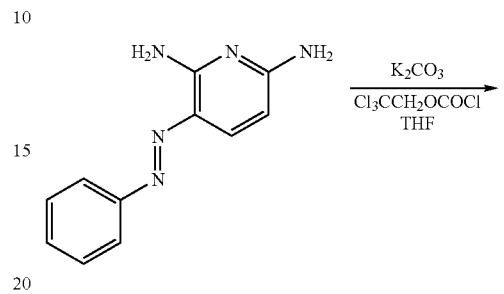

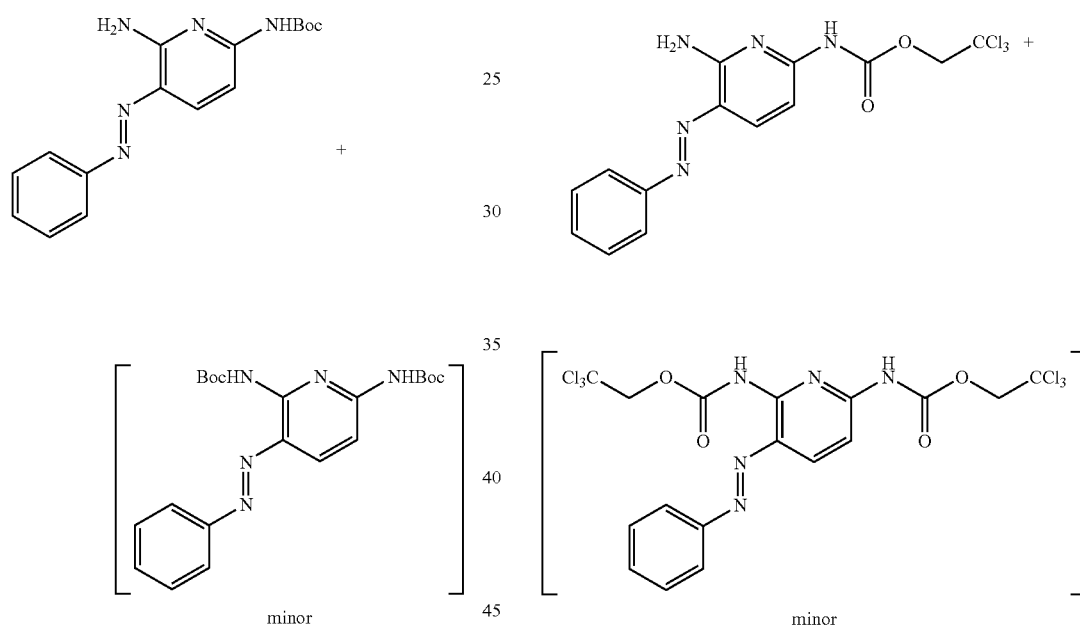

To a solution of 0.50 g (2.34 mmol) of phenazopyridine in 10 mL of THF was added 0.64 g (4.68 mmol) of oven-dried K$_2$CO$_3$ followed by a solution of 0.5 g (0.32 mL, 2.4 mmol) of trichloroethyl chloroformate in 5 mL of THF (added dropwise at room temperature over a period of 20 min.). The reaction mixture was stirred at room temperature for 4 days. The insoluble material was filtered and the solvent was concentrated under diminished pressure. The residue was purified on a silica gel column (16×3 cm), eluting with a stepwise gradient of EtOAc in hexane (0→8%). The product was obtained as a mixture of mono and bis carbamates. This mixture was fractionated on a preparative HPLC column. The mono carbamate ($R_t$ 20.3 min) was obtained as an orange solid: yield 169 mg (18%); $^1$H NMR (DMSO-d$_6$) δ 4.97 (s, 2H), 7.26 (d, 1H, J=8.4 Hz), 7.44 (m, 1H), 7.55 (t, 2H, J=7.5 Hz), 7.63 (brs, 2H), 7.87 (d, 2H, J=8.4 Hz), 8.05 (d, 1H, J=9.0 Hz) and 10.69 (s, 1H); mass spectrum (ESI) m/z 390 (M+H)$^+$ and 413 (M+Na+H)$^+$. Anal. calcd for $C_{14}H_{12}Cl_3N_5O_2$: C, 43.27; H, 3.11; N, 18.02; Cl, 27.56. Found: C, 43.50; H, 3.11;

N, 17.78; Cl; 27.56. The bis carbamate ($R_t$ 22.9 min) was obtained as an orange solid: yield 58 mg (4%); mass spectrum (ESI) m/z 564 (M)⁺.

Example 25

Preparation of n-Butylcarbamyl-phenazopyridine

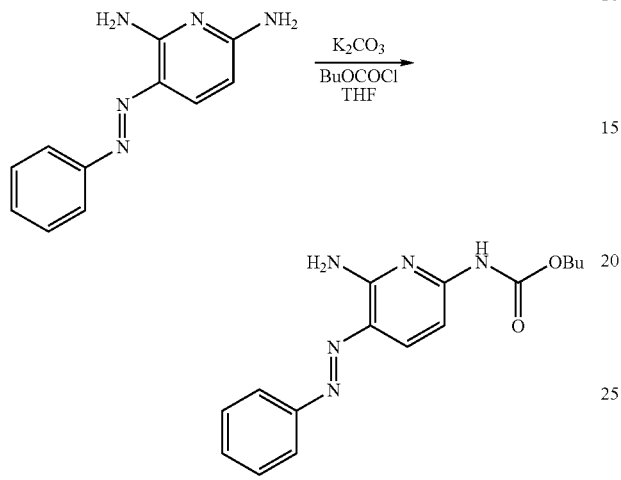

To a solution of 0.50 g (2.34 mmol) of phenazopyridine in 10 mL of THF was added 0.64 g (4.68 mmol) of oven-dried $K_2CO_3$ followed by a solution of 0.32 g (0.31 mL, 2.4 mmol) of n-butyl chloroformate in 5 mL of THF (added dropwise at room temperature over a period of 10 min). The reaction mixture was stirred at room temperature for 4 days. The insoluble material was filtered and the solvent was concentrated under diminished pressure. The residue was purified on a short pad of silica, eluting with 20% EtOAc in hexane. The product was purified further on a preparative HPLC column. The mono carbamate ($R_t$ 20.1 min) was obtained as an orange solid: yield 252 mg (34%); ¹H NMR (DMSO-$d_6$) δ 0.91 (t, 3H, J=7.2 Hz), 1.38 (m, 2H), 1.60 (m, 2H), 4.11 (t, 2H, J=5.8 Hz), 7.30 (d, 1H, J=8.7 Hz), 7.44 (m, 1H), 7.52 (t, 2H, J=7.2 Hz), 7.86 (d, 2H, J=7.2 Hz), 8.02 (d, 1H, J=8.4 Hz) and 10.09 (s, 1H); mass spectrum (ESI) m/z 314 (M+H)⁺ and 336 (M+Na)⁺. Anal. calcd for $C_{16}H_{19}N_5O_2$: C, 61.33; H, 6.11; N, 22.35. Found: C, 61.23; H, 6.11; N, 22.08.

Example 26

Preparation of $N^\alpha$-Boc-glycine Cyanomethyl Ester

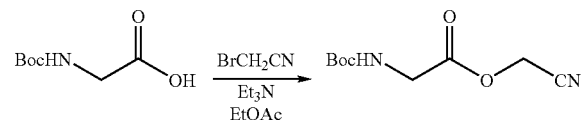

To a solution containing 2.0 g (11.4 mmol) of $N^\alpha$-Boc-glycine in 25 mL of EtOAc was added 1.73 g (2.38 mL, 17.1 mmol) of triethylamine followed by 2.05 g (1.19 mL, 17.1 mmol) of bromoacetonitrile. The reaction mixture was stirred at 60° C. under an argon atmosphere for 16 h. The heterogeneous mixture was cooled to room temperature and filtered through a short pad of silica, washing with EtOAc to remove the precipitated triethylamine hydrobromide. The filtrate was concentrated under diminished pressure to give $N^\alpha$-Boc-glycine cyanomethyl ester as a colorless syrup which solidified upon standing. The crude product was used directly in the next step without further purification: yield 2.12 g (87%); ¹HNMR (500 MHz, CDCl₃) δ 1.45 (s, 9H), 4.05 (d, 2H, J=5.5 Hz) and 4.79 (s, 2H).

Example 27

Preparation of 6-N-Boc-phenazopyridine and 2,6-N,N-bis-Boc-phenazopyridine

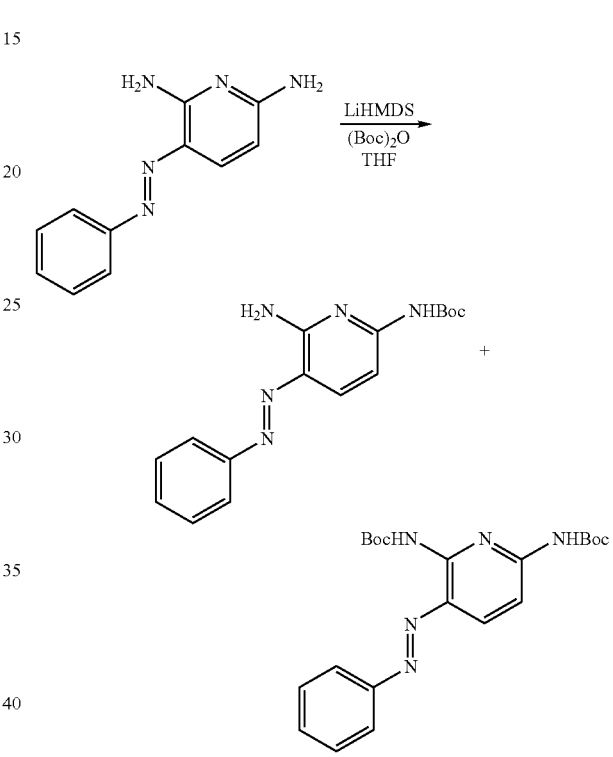

To a solution of 3.2 g (15 mmol) of phenazopyridine in 20 mL of anhydrous THF under argon atmosphere was added 30 mL (30 mmol) of a 1 M solution of LiHMDS in THF over a period of 15 min. After further 10 min, a solution of 3.27 g (15 mmol) of (Boc)₂O in 15 mL of anhydrous THF was added slowly over a period of 20 min and the reaction was allowed to proceed for a further 3 h at room temperature. The solvent was concentrated under diminished pressure and the residue was partitioned between 100 mL of dichloromethane and 100 mL of 0.1 N aqueous HCl. The organic layer was washed with two 50-mL portions of water, dried (Na₂SO₄) and concentrated under diminished pressure. Purification by chromatography on a silica gel column (20×4 cm), eluting with hexanes-ethyl acetate (7:1 and 6:1) gave successively 2,6-N,N-bis-Boc-phenazopyridine as an orange foam: yield 1.28 g (20%); silica gel TLC $R_f$ 0.44 (5:1 hexanes-ethyl acetate); ¹H NMR (500 MHz, CDCl₃) δ 1.51 (s, 9H), 1.57 (s, 9H), 7.47 (d, 1H, J=7.0 Hz), 7.52 (t, 2H, J=7.5 Hz), 7.83 (d, 2H, J=9.5 Hz), 8.15 (t, 2H, J=9.7 Hz) and 10.18 (s, 1H); mass spectrum (ESI) m/z 414 (M+H)⁺ and 436 (M+Na)⁺, then a mixture of 6-N-Boc-phenazopyridine and 2,6-N,N-bis-Boc-phenazopyridine in 8:1 ratio: yield 1.15 g, and finally 6-N-Boc-phenazopyridine: yield 0.99 g. Another 0.61 g of 6-N-Boc-phenazopyridine was recovered from the mixture by crystallization from 32 mL of 7:1 hexanes-ethyl acetate. 6-N-Boc-phenazopyridine was obtained as an orange solid: yield 1.6 g (34%); silica gel TLC $R_f$ 0.34 (5:1 hexanes-ethyl acetate); $^1$H NMR (500 MHz, CDCl$_3$) δ 1.53 (s, 9H), 7.39 (m, 1H), 7.48 (m, 3H), 7.79 (d, 2H, J=8.0 Hz) and 8.13 (d, 1H, J=8.5 Hz); mass spectrum (ESI) m/z 314 (M+H)$^+$ and 336 (M+Na)$^+$.

Example 28

Preparation of 2-N-(N$^\alpha$-Boc-glycyl)-6-N-Boc-phenazopyridine

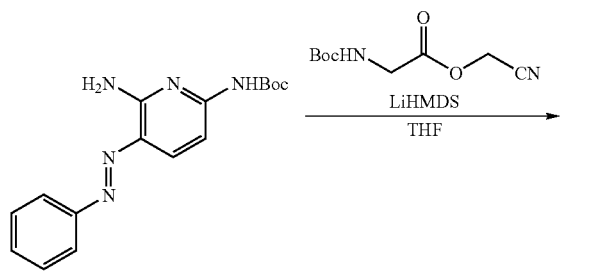

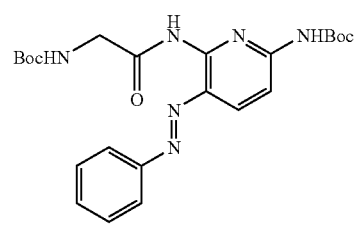

To a solution of 215 mg (0.68 mmol) of 6-N-Boc-phenazopyridine in 9 mL of anhydrous THF was added dropwise 0.69 mL (0.69 mmol) of a 1 M solution of LiHMDS in THF followed by 147 mg (0.69 mmol) of N$^\alpha$-Boc-glycine cyanomethyl ester. The reaction mixture was stirred at room temperature for 45 min. Another 0.69 mL (0.69 mmol) of a 1 M solution of LiHMDS in THF was added dropwise followed by 147 mg (0.69 mmol) of N$^\alpha$-Boc-glycine cyanomethyl ester. This procedure was repeated four more times every 45 min. and stirring was continued for another 19 h at room temperature. The reaction was quenched by slow addition of 25 mL of water and the reaction mixture was extracted with two 25-mL portions of ethyl acetate. The combined organic layer was dried (Na$_2$SO$_4$) and concentrated under diminished pressure. Purification by chromatography on a silica gel column (15×4 cm) eluting with a stepwise gradient of EtOAc in hexanes (10→50%) gave 2-N-(N$^\alpha$-Boc-glycyl)-6-N-Boc-phenazopyridine as a brown solid: yield 94 mg (29%); $^1$H NMR (500 MHz, CDCl$_3$) δ 1.47 (s, 9H), 1.55 (s, 9H), 4.56 (s, 2H), 7.47-7.53 (m, 3H), 7.83-7.88 (m, 2H), 8.17 (d, 11-1, J=9.0 Hz), 8.35 (s, 1H) and 10.40 (s, 1H); $^{13}$C NMR (125 MHz, CDCl$_3$) δ 47.04, 80.21, 81.68, 107.09, 122.71, 129,24, 129.55, 131.29, 133.06, 145.73, 152.12, 152.81, 156.22 and 169.71; mass spectrum (ESI) m/z 471 (M+H)$^+$ and 493 (M+Na)$^+$. Anal. calcd for C$_{23}$H$_{30}$N$_6$O$_5$.1.2 H$_2$O: C, 56.13; H, 6.64; N, 17.08. Found: C, 56.03; H, 6.47; N, 17.02.

Example 29

Preparation of 2-N-Glycyl-phenazopyridine Hydrochloride

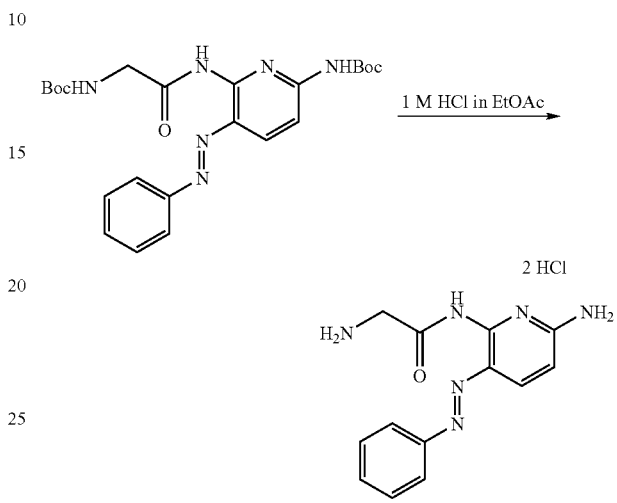

To 34 mg (0.07 mmol) of 2-N-(N$^\alpha$-Boc-glycyl)-6-N-Boc-phenazopyridine was added 2.5 mL (2.5 mmol) of a 1 M solution of HCl in EtOAc. The reaction mixture was stirred at 65° C. for 2.5 h. Another 2 mL (2 mmol) of 1 M HCl in EtOAc was added and stirring was continued at 65° C. for another 45 min. The precipitated product was filtered, washed with two 5-mL portions of EtOAc and dried under vacuum for 24 h. 2-N-Glycyl-phenazopyridine hydrochloride was obtained as a brown solid: yield 20.8 mg (84%); $^1$H NMR (DMSO-d$_6$, 500 MHz) δ 4.16 (d, 2H, J=5.0 Hz), 6.49 (d, 1H, J=9.0 Hz), 7.45 (m, 1H), 7.51 (m, 2H), 7.87 (d, 2H, J=9.0 Hz), 7.96 (d, 1H, J=9.0 Hz) and 8.30 (br s, NH); $^{13}$C NMR (DMSO-d$_6$, 125 MHz) δ 42.70, 106.90, 122.88, 128.01, 129.36, 129.66, 130.60, 148.10, 152.62, 160.15 and 167.58; mass spectrum (ESI) m/z 271 (M+H)$^+$, 272 (M+2H)$^+$, 293 (M+Na)$^+$.

Example 30

Oral Bioavailability of PAP Prodrug in Rats

The oral bioavailability of PAP (phenazopyridine) prodrugs was evaluated in healthy rats. All the PAP amide (amino acid derivatives) bases were dissolved in 0.1N HCl (the same result can be obtained with a lower molarity), while the carbamates were dissolved in PEG-400 due to the very poor aqueous solubility of the PAP-carbamates. The physicochemical properties of various PAP derivatives are shown in Table 1. In general, all of the amino acid amide derivatives of PAP had higher water solubility than those of the PAP-carbamates. In another PK study, PAP.HCl salt, Gly-PAP.HCl salt and Gly-PAP.mesylate salt were dissolved in water, affording a clear solution in each case prior to oral administration.

The rats were fasted overnight prior to dosing. Appropriate amount of each compound was administered via gastric gavages, and at predetermined time (1, 2, 4, 6, and 24 h) blood samples were withdrawn from the rats. The whole blood was centrifuged immediately, and supernatant (plasma) was collected. The plasma samples were assayed for PAP using LC-MS-MS.

TABLE 1

Physicochemical properties of PAP-prodrug and administered oral dose in rats

| Compound's Generic name | Mol. Wt. (g/mol) | Solubility in 0.1 N HCl (mg/mL) | Oral Dose, mg/kg prodrug | PAP free-base equivalent |
|---|---|---|---|---|
| PAP · HCl | 249.7 | 0.5 | 10.0 | 8.5 |
| Gly-PAP | 270.3 | >2 | 13.4 | 10.6 |
| Alanyl-PAP | 284.3 | 2 | 14.2 | 10.6 |
| Methionyl-PAP | 344.4 | 1 | 10.0 | 6.2 |
| Ethylcarbamyl-PAP | 285.3 | <0.1 | 13.4 | 10.0 |
| Benzylcarbamyl-PAP | 347.4 | <0.1 | 8.2 | 5.0 |
| Isobutylcarbamyl-PAP | 313.4 | <0.1 | 7.4 | 5.0 |
| Histidinyl-PAP | 350.4 | >10 | 8.2 | 5.0 |
| Tryptophanyl-PAP | 399.0 | 0.5 | 9.4 | 5.0 |
| Valyl-PAP | 312.0 | >2.5 | 14.6 | 10.0 |
| Lysyl-PAP | 341.0 | >2.5 | 16.0 | 10.0 |

TABLE 2

Pharmacokinetic analysis of PAP prodrugs following oral administration in rats

| Compound | Actual Dose (mg/kg) | PAP-free base equivalent (mg/kg) | $C_{max}$ (ng/mL) | $T_{max}$ (h) | $AUC_{0-24}$ (ng · h/mL) | Relative Bioavailability (%) |
|---|---|---|---|---|---|---|
| PAP•HCl | 10 | 8.5 | 54 | <1 | 182 ± 12 | 100 |
| Gly-PAP | 13.6 | 10 | 344 | <1 | 2235 ± 132 | 985 |
| Alanyl-PAP | 14.4 | 10 | 173 | <1 | 511 ± 41 | 225 |
| Methionyl-PAP | 10 | 5.9 | 80 | <1 | 193 ± 46 | 145 |
| Ethylcarbamyl-PAP | 13.4 | 10 | BQL | ND | 0 | 0 |
| Isobutylcarbamyl-PAP | 7.4 | 5 | 8.6 | 6 | 136 ± 25 | 127 |
| Benzylcarbamyl-PAP | 8.2 | 5 | 8 | <1 | 65 ± 7 | 61 |
| Histidinyl-PAP | 8.2 | 5 | 13.7 | <1 | 172 ± 3.4 | 161 |
| Tryptophanyl-PAP | 9.4 | 5 | 17.1 | 2 | 145 ± 4.6 | 135 |
| Valyl-PAP | 14.6 | 10 | 213 | 0.5 | 225 ± 25 | 105 |
| Lysyl-PAP | 16.0 | 10 | 249 | 0.5 | 821 ± 97 | 383 |

AUC: area under curve of plot plasma concentration vs. time, 0-24 hr
Relative Bioavailability (%) = [AUC(prodrug)/AUC(drug) × Dose(drug)/Dose(prodrug)] 100
BQL: below quantitation limit (<0.5 ng/mL)
$C_{max}$: peak plasma concentration
$T_{max}$: time to reach peak plasma concentration ($C_{max}$)

The pharmacokinetics data is summarized in Table 2. The relative bioavailability of PAP prodrug was in the following order:
glycine>lysine>alanine>histidine>methionine>tryptophan>valine>isobutylcarbamyl>benzylcarbamyl>ethylcarbamyl. $T_{max}$ was longer for isobutylcarbamyl-PAP and tryptophanyl-PAP, while the $T_{max}$ for the rest of PAP derivatives were less than an hour.

The pharmacokinetics data for various salt forms of Gly-PAP is shown in Table 3. The free base of Gly-PAP, as well as the HCl and mesylate salts, have significantly enhanced bioavailability as compared with the HCl salt of PAP.

The pharmacokinetics data for various salt forms of Gly-PAP is shown in Table 3. The free base of Gly-PAP, as well as the HCl and mesylate salts, have significantly enhanced bioavailability as compared with the HCl salt of PAP.

TABLE 3

PAP Pharmacokinetics in rats following oral administration of PAP•HCl salt, Gly-PAP freebase, Gly-PAP•HCl salt, and Gly-PAP•mesylate salt

| Compounds | Vehicle used to dissolve compound | Dose (mg/kg, PAP base equivalent) | $C_{max}$ (ng/ml) | $T_{max}$ (h) | $AUC_{0-6}$ (ng · h/mL) (SD) | $T_{1/2}$ (h) |
|---|---|---|---|---|---|---|
| PAP•HCl | Water | 2.5 | 58 | 0.25 | 105 (20) | 0.8 |
| Gly-PAP•HCl | Water | 2.5 | 140 | 1.0 | 433 (12) | 1.5 |
| Gly-PAP•mesylate | Water | 2.5 | 102 | 1.0 | 237 (51) | 1.6 |
| Gly-PAP•free base | 0.1 N HCl | 2.8 | 211 | 0.5 | 378 (57) | 1.7 |

Example 31

Alternative Synthesis of 2-Amino-6-aminoacetamido-3-E-phenazopyridine Dihydrochloride

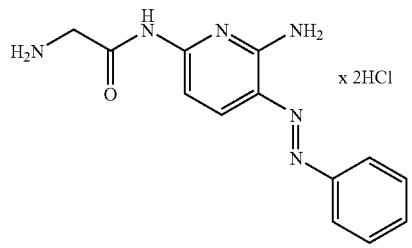

Chemical formula: $C_{13}H_{16}Cl_2N_6O$

Molecular Weight: 343.21

Figure 16:
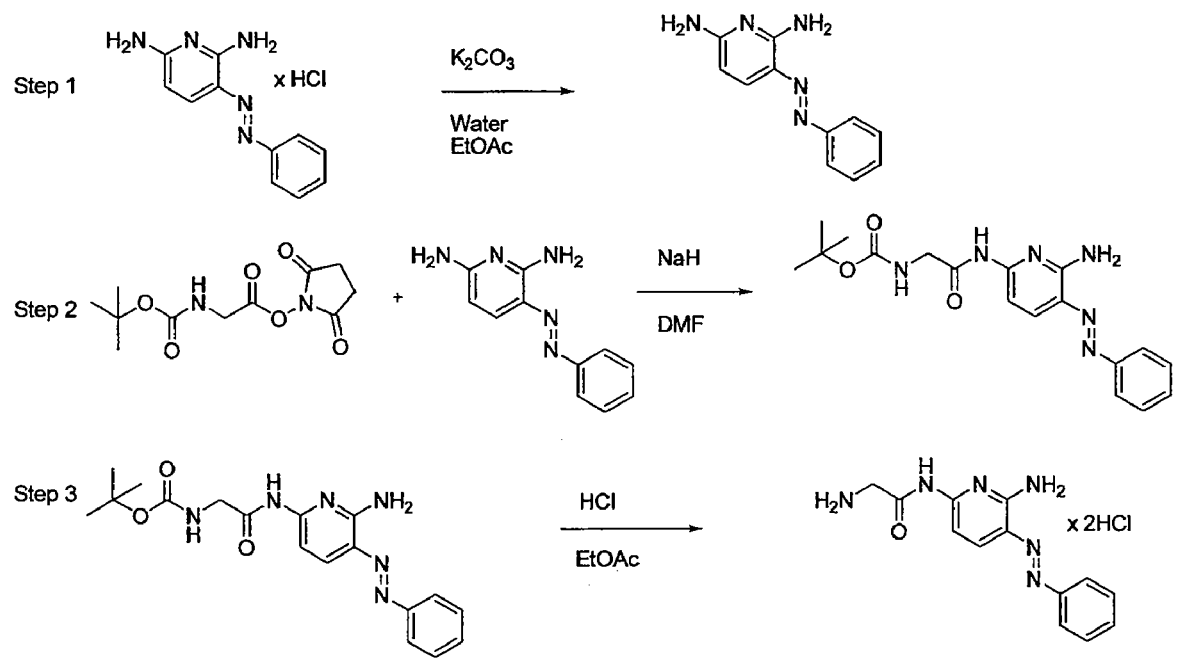
FIG. 16 is a synthetic scheme for production of 2-amino-6-aminoacetamido-3-E-phenazopyridine dihydrochloride.

Description of Manufacturing Process depicted in FIG. 16. Gly-PAP is an amide prodrug of phenazopyridine with the carboxyl group of glycine covalently bound to the nitrogen of the 6-amine of phenazopyridine.

In the first step of the production of Gly-PAP, phenazopyridine hydrochloride (PAP) was converted to the free base using aqueous potassium carbonate. The free base was extracted into ethyl acetate and isolated by concentration of the solvent in 92% yield. In the second step of the process, phenazopyridine free base was treated with BOC-glycine-OSu in DMF using sodium hydride as the base. The intermediate was isolated by adding water to the reaction mixture which caused the product to precipitate. The product was isolated by filtration, washed with water and recrystallized from isopropyl alcohol to give the intermediate in 34% yield. In the third step BOC-Gly-PAP was deprotected by treatment with HCl in ethyl acetate. The product was isolated in 96% yield by filtration, followed by washing with ethyl acetate and drying at 45° C. under vacuum.

EXPERIMENTAL PROCEDURES

Preparation of Phenazopyridine Free Base from the HCl Salt

To a solution of 27.6 grams (200 mmol) of potassium carbonate in 200 mL of water was added 20.0 grams (80 mmol) of phenazopyridine hydrochloride followed by 200 mL of ethyl acetate. The mixture was stirred at room temperature for 30 minutes. The layers were separated and the aqueous layer was extracted one time with 100 mL of ethyl acetate. The ethyl acetate layer was dried over sodium sulfate, and filtered. The filtrate was concentrated under diminished pressure and the product was dried under vacuum at room temperature to give an orange solid: yield 15.1 grams (92%). NMR (300 MHz, $CDCl_3$) δ 4.80 (br s, 4H), 6.06 (d, 1H), 7.34 (m, 1H), 7.48 (m, 2H), 7.76 (m, 2H), and 7.93 (d, 1H).

Treatment of Phenazopyridine Free Base with N-Boc-Glycine Succinimide Ester

To a suspension of 5.39 g (224.5 mmol) of NaH in 500 mL DMF maintained at 0-5° C. was added dropwise a solution of 16.0 g (74.40 mmol) of phenazopyridine in 250 mL of DMF and the reaction was stirred at 0-5° C. for 30 min. N-Boc-glycine succinimide ester (25.4 g, 93.50 mmol) in DMF (190 mL) was added dropwise at 0-5° C. then the mixture was warmed to room temperature and stirred for 1.5 h. Isopropyl alcohol (25 mL) was added dropwise and the mixture was stirred at room temperature for 15 min. To the reaction mixture was added 60 grams of Celite™ and it was stirred for 15 minutes. The reaction mixture was filtered and the filter cake was washed two times with 100 mL of DMF. Water (2,500 mL) was added to the DMF solution causing an orange solid to precipitate. The mixture was stirred at room temperature for 30 minutes then the precipitated product was filtered, washed with four 250 mL portion of water and then dried under vacuum over $P_2O_5$ at 45° C. for 18 h. The crude product was obtained as an orange powder: yield 12.63 g (46%), purity 95.9% by HPLC.

The crude product (12.63 grams, 34.1 mmol) was dissolved in 170 mL iPrOH at 80° C. to form a clear dark orange solution. It was cooled slowly to room temperature and then to 0-5° C. The crystallized product was collected by filtration and dried under vacuum over $P_2O_5$ at 45° C. for 2 hours. The product, BOC-glycine-phenazopyridine, was obtained as a light orange solid: yield 9.4 g (74%), purity 98.2% by HPLC. Overall yield 34%. $^1$H NMR (300 MHz, $CDCl_3$) δ 1.58 (s, 9H), 4.00 (d, 2H, J=4 Hz), 7.47 (m, 4H), 7.80 (m, 2H), 8.17 (d, 1H, J=9 Hz), and 8.29 (br s, 1H).

Deprotection of Boc-Glycine-Phenazopyridine to Form Gly-Pap Dihydrochloride

To a solution of 9.3 grams (25.1 mmol) of BOC-glycine-phenazopyridine in 236 mL of ethyl acetate was bubbled HCl gas generated by adding concentrated HCl (46 mL, 55.2 grams, 1.53 moles) to 133 mL of concentrated sulfuric acid in a separate flask. After the addition of HCl was complete, the reaction mixture was stirred at room temperature for 3.5 hours. The solid that was formed was isolated by filtration and was washed with 500 mL of ethyl acetate. The product was dried under full vacuum at room temperature to give 8.4 grams of Gly-PAP as an orange solid: yield 98.1%, 98.9% purity by HPLC. $^1$H NMR (300 MHz, $D_2O$) δ 3.8 (s, 2H), δ 6.5 (d, 1H), δ 7.3 (br s, 3H), δ 7.6 (br s, 2H), δ 8.0 (d, 1H)

Raw Materials and Reagents

| Raw Material/Reactant | Supplier Part number (P/N) | Purity | CAS number |
|---|---|---|---|
| Phenazopyridine hydrochloride | Spectrum Chemicals P/N: P1059 | >99% | 136-40-3 |
| Boc-glycine-OSu | Chem-Impex International P/N: 03793 | 99% | 3392-07-02 |
| Sodium hydride | Aldrich P/N: 223441 | 95% | 7646-69-7 |
| DMF | Sigma-Aldrich P/N: 227056 | 99.8% | 68-12-2 |
| Isopropanol | EMD Chemicals P/N: PX1834-1 | 99.9% | 67-63-0 |
| HCl (Conc.) | Fisher Scientific P/N: A144-212 | 37.0% | 7647-01-1 |
| Ethyl acetate | Fisher Scientific P/N: E195-4 | 99.9% | 141-78-6 |
| $H_2SO_4$ (Conc.) | Fisher Scientific P/N: A484-212 | 96.1% | 7664-93-9 |

Example 32

Oral Bioavailability of PAP and Gly-PAP (Improved Bioavailability, Limited Gly-PAP Exposure, Sustained Release of PAP from Gly-PAP, Increased Delivery to Site of Action Pharmacokinetics for PAP and Gly-PAP (intact prodrug) were assessed in male rats following administration by oral gavage of mg/kg doses. Rats were fasted overnight prior to dosing. Blood samples were withdrawn at 0.25, 0.5, 1, 2, 4, 6, and 24 hours. The whole blood was centrifuged immediately, and supernatant (plasma) was collected. The plasma samples were assayed for PAP and Gly-PAP by LC-MS-MS.

At a Gly-PAP dose of 4.0 mg/kg (containing 2.5 mg/kg phenazopyridine base approximating 30 mg of a phenazopyridine HCl human equivalent dose (HED*), an increase of roughly 3-fold was observed for phenazopyridine from Gly-PAP compared to the equivalent phenazopyridine hydrochloride dose (2.5 phenazopyridine base content). Plasma levels of Gly-PAP were <5% of those for phenazopyridine from Gly-PAP, illustrating efficient hydrolysis of Gly-PAP with limited systemic exposure to the prodrug. Results are illustrated in FIGS. 1, 3, 4, 11, and 12.

Figure 3:
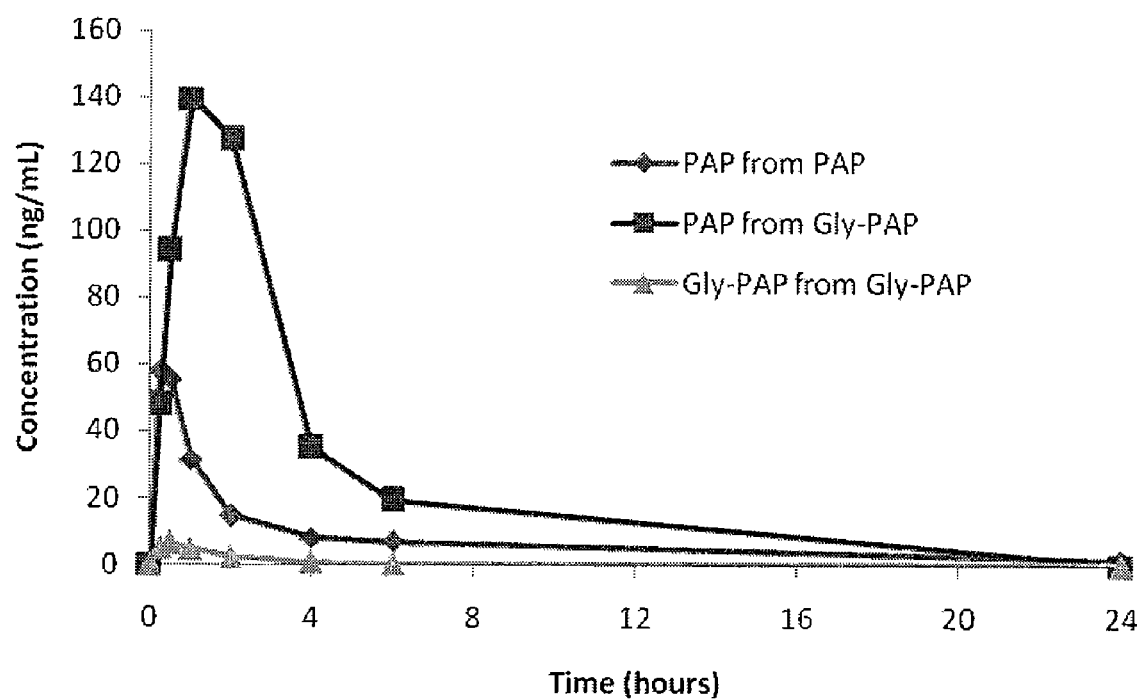
FIG. 3 is a graph showing mean rat (male) plasma concentration curves of 1) phenazopyridine from phenazopyridine hydrochloride (2.8 mg/kg containing 2.5 mg/kg phenazopyridine base), 2) phenazopyridine from Gly-PAP (4 mg/kg, containing 2.5 mg/kg phenazopyridine base), and 3) Gly-PAP intact prodrug from Gly-PAP (4 mg/kg, containing 2.5 mg/kg phenazopyridine base).
Figure 4:
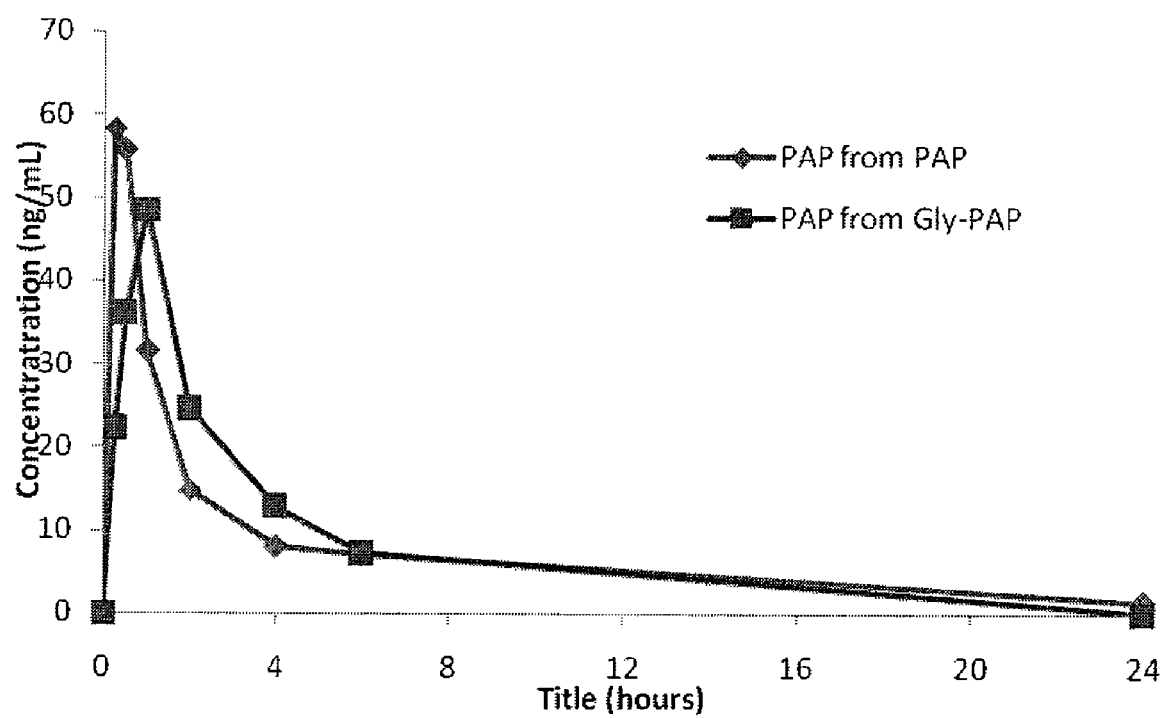
FIG. 4 is a graph showing mean rat (male) plasma concentration curves of 1) phenazopyridine from phenazopyridine hydrochloride (2.8 mg/kg containing 2.5 mg/kg phenazopyridine base) and 2) phenazopyridine from Gly-PAP (0.9 mg/kg, containing 0.6 mg/kg phenazopyridine base).

Pharmacokinetics for phenazopyridine for Gly-PAP were determined for a lower dose of 0.9 mg/kg Gly-PAP (0.6 mg/kg phenazopyridine base). When plotted with concentrations of phenazopyridine from an approximately 4-fold higher dose of 2.8 mg/kg phenazopyridine HCl (2.5 mg/kg phenazopyridine base) the lower Gly-PAP dose afforded sustained release of phenazopyridine and approximately equal AUC (FIGS. 3 and 12).

When compared to levels of phenazopyridine following oral administration of 100, 200 and 300 mg in humans (approximate human equivalent dose (HED) based on 60 kg person (6.2 rat conversion factor)—Guidance for Industry: Estimating the Maximum Safe Starting Dose for Initial Clinical Trials for Therapeutics in Adult Healthy Volunteers), the levels of phenazopyridine where considerably higher in rats at HEDs of approximately 100 mg or less for both Gly-PAP and phenazopyridine hydrochloride. Although the absolute bioavailability of phenazopyridine hydrochloride in humans has not been determined it appears to be poorly absorbed. (Shang E, et al. *Determination of phenazopyridine in human plasma via LC-MS and subsequent development of a pharmacokinetic model. Anal Bioanal Chem.* 2005 May; 382(1): 216-22). Rat pharmacokinetics have been found to be highly correlated with human pharmacokinetics. (See Chiou, W. L, et al., *Pharm. Res.* 17:135-140 (2000); Chiou, W. L., et al., *Pharm. Res.* 15:1474-1479 (1998); and Chiou, W. L., et al., *J. Clin. Pharmacol. Ther.* 38:532-539 (2000).

Pharmacokinetics for PAP and Gly-PAP (intact prodrug) were assessed in dogs following administration by oral gavage of mg/kg doses. Blood (approximately 2 mL) was collected from a jugular vein into tubes containing lithium heparin anticoagulant predose and at 0.083, 0.25, 0.5, 1, 2, 4, 8, 12, and 24 hours postdose. Urine was collected into plastic containers surrounded by wet ice predose (−18 to 0) and 0 to 24 hours postdose. The volume of each sample was recorded. Plasma and urine samples were assayed for PAP and Gly-PAP by LC-MS-MS.

Figure 13:
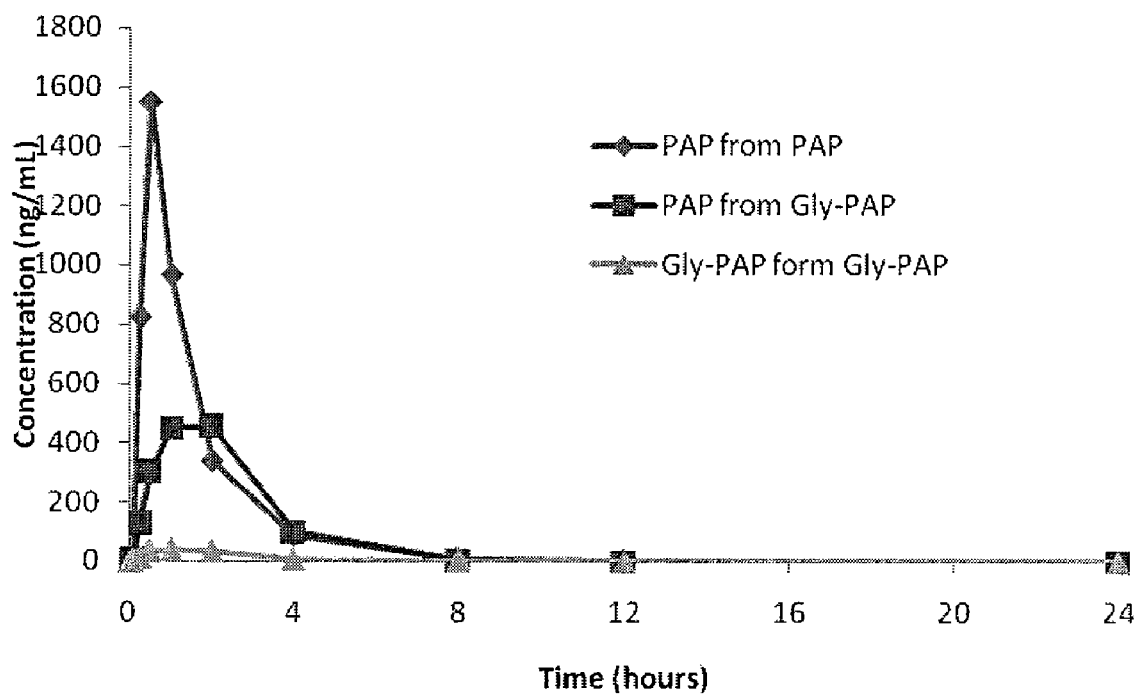
FIG. 13 is a graph showing mean dog (male) plasma concentration curves of 2) phenazopyridine from phenazopyridine hydrochloride (5.9 mg/kg containing 5 mg/kg phenazopyridine base), 2) phenazopyridine from Gly-PAP (8.1 mg/kg, containing 5 mg/kg phenazopyridine base), and 3) Gly-PAP intact prodrug from Gly-PAP (8.1 mg/kg, containing 5 mg/kg phenazopyridine base).

In dogs Gly-PAP afforded effective delivery of phenazopyridine following oral administration of 8.1 mg/kg Gly-PAP, approximating a HED (Approximate human equivalent dose (HED) based on 60 kg person (1.8 dog conversion factor—Guidance for Industry: Estimating the Maximum Safe Starting Dose for Initial Clinical Trials for Therapeutics in Adult Healthy Volunteers) of 200 mg of phenazopyridine HCl. Phenazopyridine from phenazopyridine HCl containing an equivalent amount of phenazopyridine resulted in greater plasma bioavailability of phenazopyridine; however, a greater amount of phenazopyridine was delivered to the urine from Gly-PAP. The site of action for phenazopyridine is the bladder and urethra. Plasma $T_{max}$ was increased for phenazopyridine from Gly-PAP as compared to phenazopyridine from phenazopyridine HCl, illustrating sustained release. Exposure ($AUC_{0-24}$) to Gly-PAP was less than 10% of that for phenazopyridine in dogs following administration of Gly-PAP (FIGS. 13-15).

The pharmacokinetics of various salts of Gly-PAP were compared following oral administration to rats. All salt forms improved the oral bioavailability of phenazopyridine as compared to bioavailability from phenazopyridine HCl. Gly-PAP HCl afforded the highest bioavailability (FIG. 17).

Example 33

Reduced Emesis in Dogs

Dogs (1 male/1 female) were dosed by oral gavage 3 times (TID), once every 8 hours, with 40 mg/kg Gly-PAP or 29 mg/kg phenazopyridine HCl (doses contained an equivalent amount of 24.8 mg/kg phenazopyridine base). A single observation of vomitus was observed for Gly-PAP compared to four observations of vomitus for phenazopyridine HCl. Results showing reduction of the GI side effect of emesis are illustrated in FIG. 18.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:
1. A compound of Formula I:

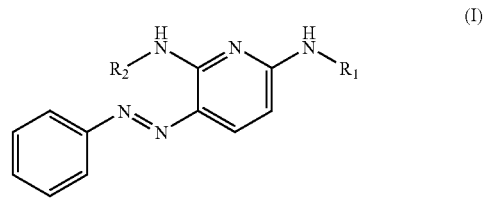

wherein,
$R_1$ and $R_2$ are independently
  (a) hydrogen;
  (b) the residue of an amino acid or peptide;
  (c)

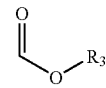

wherein $R_3$ is an optionally substituted alkyl or arylalkyl; or
  (d) the residue of an amino acid wherein the amine of the amino acid is protected with a t-butylcarbonyl;
wherein at least one of $R_1$ and $R_2$ is other than hydrogen.

2. The compound of claim 1, wherein $R_1$ is an amino acid residue and $R_2$ is hydrogen.

3. The compound of claim 1, wherein $R_1$ is an (L-) amino acid residue and $R_2$ is hydrogen.

4. The compound of claim 2, wherein the amino acid residue is selected from the group consisting of the residues of alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine.

5. The compound of claim 3, wherein the (L-) amino acid residue is selected from the group consisting of the residues of alanine, arginine, asparagine, aspartic acid, cysteine, glutamic acid, glutamine, histidine, isoleucine, leucine, lysine, methionine, proline, phenylalanine, serine, tryptophan, threonine, tyrosine, and valine.

6. The compound of claim 1, wherein $R_1$ is the amino acid residue of glycine and $R_2$ is hydrogen.

7. The compound of claim 1, wherein $R_1$ is the amino acid residue of lysine and $R_2$ is hydrogen.

8. The compound of claim 1, wherein $R_1$ is the amino acid residue of alanine and $R_2$ is hydrogen.

9. The compound of claim 1, wherein $R_1$ is (c), $R_3$ is selected from the group consisting of ethyl, benzyl, isobutyl, dodecyl, ethylhexyl, trichloroethyl, and n-butyl, and $R_2$ is hydrogen.

10. The compound of claim 1, wherein $R_2$ is an amino acid residue and $R_1$ is hydrogen.

11. The compound of claim 1, wherein $R_2$ is an (L-) amino acid residue and $R_1$ is hydrogen.

12. The compound of claim 10, wherein the amino acid residue is selected from the group consisting of the residues of alanine, arginine, asparagine, aspartic acid, cysteine, glycine, glutamic acid, glutamine, histidine, isoleucine, leucine, lysine, methionine, proline, phenylalanine, serine, tryptophan, threonine, tyrosine, and valine.

13. The compound of claim 11, wherein the (L-) amino acid residue is selected from the group consisting of the residues of alanine, arginine, asparagine, aspartic acid, cysteine, glutamic acid, glutamine, histidine, isoleucine, leucine, lysine, methionine, proline, phenylalanine, serine, tryptophan, threonine, tyrosine, and valine.

14. The compound of claim 1, wherein $R_2$ is the amino acid residue of glycine and $R_1$ is hydrogen.

15. The compound of claim 1, wherein $R_2$ is the amino acid residue of lysine and $R_1$ is hydrogen.

16. The compound of claim 1, wherein $R_2$ is the amino acid residue of alanine and $R_1$ is hydrogen.

17. The compound of claim 1, wherein $R_2$ is (c), $R_3$ is selected from the group consisting of ethyl, benzyl, isobutyl, dodecyl, ethylhexyl, trichloroethyl, and n-butyl, and $R_2$ is hydrogen.

18. A pharmaceutical composition comprising a therapeutically effective amount of the compound of claim 1.

19. The pharmaceutical composition of claim 18, wherein the therapeutically effective amount of the compound is less than 50% of the therapeutically effective amount of an unconjugated phenazopyridine.

20. A method for the treatment of urinary tract pain, burning, irritation, discomfort, or urgent or frequent urination caused by urinary tract infections, surgery, injury, or examination procedures comprising administering a therapeutically effective amount of the compound of claim 1.

21. The method of claim 20, wherein the therapeutically effective amount of the compound is less than 50% of the therapeutically effective amount of an unconjugated phenazopyridine.

22. The method of claim 20, wherein the side effects of the administration of the compound are reduced by at least 10% relative to the side effects of the administration of unconjugated phenazopyridine.

23. A pharmaceutical composition comprising a therapeutically effective amount of glycyl-phenazopyridine.

24. A pharmaceutical composition comprising a therapeutically effective amount of alanyl-phenazopyridine.

25. A pharmaceutical composition comprising a therapeutically effective amount of lysyl-phenazopyridine.

26. The pharmaceutical composition as in any one of claims 23, 24, and 25, wherein the therapeutically effective amount of the compound is less than 30% of the therapeutically effective amount of an unconjugated phenazopyridine.

27. The pharmaceutical composition as in any one of claims 23, 24, and 25, wherein the therapeutically effective amount of the compound is less than 50% of the therapeutically effective amount of an unconjugated phenazopyridine.

28. The pharmaceutical composition as in any one of claims 23, 24, and 25, wherein the therapeutically effective amount of the compound is less than 70% of the therapeutically effective amount of an unconjugated phenazopyridine.

29. A method for the treatment of urinary tract pain, burning, irritation, discomfort, or urgent or frequent urination caused by urinary tract infections, surgery, injury, or examination procedures comprising administering a therapeutically effective amount of glycyl-phenazopyridine.

30. A method for the treatment of urinary tract pain, burning, irritation, discomfort, or urgent or frequent urination caused by urinary tract infections, surgery, injury, or examination procedures comprising administering a therapeutically effective amount of alanyl-phenazopyridine.

31. A method for the treatment of urinary tract pain, burning, irritation, discomfort, or urgent or frequent urination caused by urinary tract infections, surgery, injury, or examination procedures comprising administering a therapeutically effective amount of lysyl-phenazopyridine.

32. The method as in any one of claims 29, 30, and 31, wherein the side effects of the administration of the compound are reduced by at least 10% relative to the side effects of the administration of an unconjugated phenazopyridine.

33. The pharmaceutical composition as in any one of claims 23, 24, and 25, wherein the phenazopyridine is a hydrochloride salt.

* * * * *